US009073934B2

(12) United States Patent
Scammells et al.

(10) Patent No.: US 9,073,934 B2
(45) Date of Patent: Jul. 7, 2015

(54) METHOD FOR THE N-DEMETHYLATION OF N-METHYL HETEROCYCLES

(75) Inventors: Peter John Scammells, North Balwyn (AU); Gaik Orbell, North Carlton (AU)

(73) Assignee: MONASH UNIVERSITY, Clayton (AU)

( * ) Notice: Subject to any disclaimer, the term of this patent is extended or adjusted under 35 U.S.C. 154(b) by 443 days.

(21) Appl. No.: 13/496,562

(22) PCT Filed: Sep. 16, 2010

(86) PCT No.: PCT/AU2010/001204
§ 371 (c)(1),
(2), (4) Date: May 23, 2012

(87) PCT Pub. No.: WO2011/032214
PCT Pub. Date: Mar. 24, 2011

(65) Prior Publication Data
US 2012/0226043 A1    Sep. 6, 2012

(30) Foreign Application Priority Data

Sep. 16, 2009 (AU) .............................. 2009904493

(51) Int. Cl.
| C07D 489/08 | (2006.01) |
| C07D 451/02 | (2006.01) |
| C07B 37/06 | (2006.01) |
| C07D 451/00 | (2006.01) |
| C07D 451/06 | (2006.01) |
| C07D 451/10 | (2006.01) |
| C07D 489/00 | (2006.01) |
| C07D 489/02 | (2006.01) |

(52) U.S. Cl.
CPC .............. *C07D 489/08* (2013.01); *C07B 37/06* (2013.01); *C07D 451/00* (2013.01); *C07D 451/06* (2013.01); *C07D 451/10* (2013.01); *C07D 489/00* (2013.01); *C07D 489/02* (2013.01)

(58) Field of Classification Search
USPC ............................................ 546/45, 44, 124
See application file for complete search history.

(56) References Cited

U.S. PATENT DOCUMENTS

| 5,559,233 A | 9/1996 | Bernhart et al. |
| 2009/0005564 A1 | 1/2009 | Carroll et al. |

FOREIGN PATENT DOCUMENTS

| EP | 2062897 A1 | 5/2009 |
| WO | WO-02/16367 A1 | 2/2002 |
| WO | WO-2009/003272 A1 | 1/2009 |

OTHER PUBLICATIONS

Thavaneswaran and Scammells, "Further investigation of the N-demethylation of tertiary amine alkaloids using the non-classical Polonovski reaction," *Bioorg. Med. Chem. Lett.*, 16:2868-2871 (2006).
Barry et al., "Products and Mechanisms in the Anodic Oxidation of N,N-Dimethylbenzylamine in Methanol," *J. Org. Chem.*, 39(18):2695-2699 (1974).
Berényi et al., "Recent Developments in the Chemistry of Thebaine and its Transformation Products as Pharmacological Targets," *Current Medicinal Chemistry*, 16:3215-3242 (2009).
Caldwell et al., "Configurational Analysis of Thebaine, Codeine and 14β-Hydroxycodeinone N-Oxides," *Magnetic Resonance in Chemistry*, 34:505-511 (1996).
Carroll et al., "Palladium-Catalyzed N-Demethylation/N-Acylation of Some Morphine and Tropane Alkaloids," *Advanced Synthesis & Catalysis*, 350:2984-2992 (2008).
Chaudhary et al., "Biotransformations of Morphine Alkaloids by Fungi: N-Demethylations, Oxidations, and Reductions," *Collection of Czechoslovak Chemical Communications*, 74:1179-1193 (2009).
Cooley and Evain, "Amine Dealkylations with Acyl Chlorides," *Synthesis*, pp. 1-7 (1989).
Dong and Scammells, "New Methodology for the N-Demethylation of Opiate Alkaloids," *J. Org. Chem.*, 72:9881-9885 (2007).
Ferris et al., "Detoxication Mechanisms. II. The Iron-Catalyzed Dealkylation of Trimethylamine Oxide$^{1-3}$," *J. Am. Chem. Soc.*, 89:5270-5275 (1967).
Iijima et al., "Studies in the (+)-Morphinan Series. 5.$^1$ Synthesis and Biological Properties of (+)-Naloxone," *J. Med. Chem.*, 21(4):398-400 (1978).
Kok et al., "An Improved Process for the N-Demethylation of Opiate Alkaloids Using an Iron(II) Catalyst in Acetate Buffer," *Adv. Synth. Catal.*, 351:283-286 (2009).
Madyastha and Reddy, "*Mucor piriformis*, An Efficient N-Dealkylating Reagent for Thebaine and its N-Variants," *J. Chem. Soc., Perkin Transactions 1*, pp. 911-912 (1994).
Madyastha, "Preparatively useful transformations of steroids and morphine alkaloids by *Mucor piriformis*," *Proc. Indian Acad. Sci. (Chem. Sci.)*, 106(5):1203-1212 (1994).
McCamley et al., "Efficient N-Demethylation of Opiate Alkaloids Using a Modified Nonclassical Polonovski Reaction," *J. Org. Chem.*, 68:9847-9850 (2003).
Merz and Pook, "Reaktionen des Thebains mit Azodicarbonsäureestern"("Reactions of Thebaines with azodicarboxylates"), *Tetrahedron*, 26:1727-1741 (1970).
Rice, "An Improved Procedure for the N-Demethylation of 6,7-Benzomorphans, Morphine, and Codeine," *J. Org. Chem.*, 40(12):1850-1851 (1975).
Rice and May, "Procedural Refinements in the N-Demethylation of Morphine and Codeine Using Phenyl Chloroformate and Hydrazine," *J. Heterocyclic Chemistry*, 14:665-666 (1977).

(Continued)

*Primary Examiner* — Charanjit Aulakh
(74) *Attorney, Agent, or Firm* — McCarter & English, LLP; Elizabeth A. Hanley, Esq.; Yu Lu

(57) ABSTRACT

The present invention provides methods of N-demethylating, N-methylated heterocycles and N-methyl, N-oxide heterocycles using a transition metal with an oxidation state of zero, ferrocene or substituted derivatives thereof, or $Cr^{3+}$. N-demethylated heterocycles prepared by the methods of the present invention are also provided.

20 Claims, 1 Drawing Sheet

(56) References Cited

OTHER PUBLICATIONS

Ripper et al., "Photochemical *N*-Demethylation of Alkaloids," *Bioorganic & Medicinal Chemistry Letters*, 11:443-445 (2001).
Schwab, "14-(Arylhydroxyamino)codeinones and Derivatives as Analgetics and Antagonists," *J. Med. Chem.*, 23:698-702 (1970).
Smith and Mann, "Electrochemical Dealkylation of Aliphatic Amines," *J. Org. Chem.*, 34:1821-1826 (1969).
Thavaneswaran et al., "N-Demethylation of Alkaloids," *Natural Product Communications*, 1:885-897 (2006).
Von Braun, "Die Aufspaltung cyclischer Basen durch Bromcyan"("The splitting of cyclic bases by cyanogen bromide"), *Chemische Berichte*, 42:2035-2057 (1909).
Zhang et al., "Synthesis of 2-Fluoro-11-hydroxy-*N*-propylnoraporphine: A Potential Dopamine $D_2$ Agonist," *Organic Letters*, 7:3239-3242 (2005).

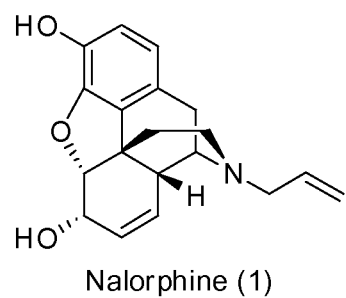
Nalorphine (1)
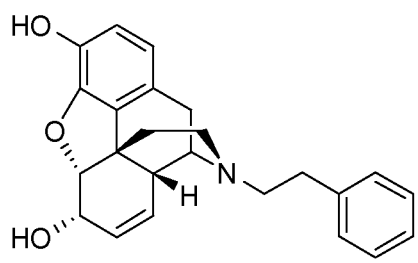
2
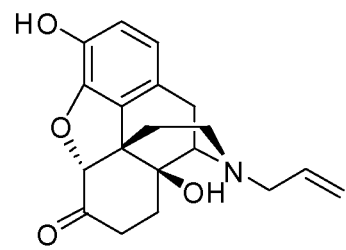
Naloxone (3)
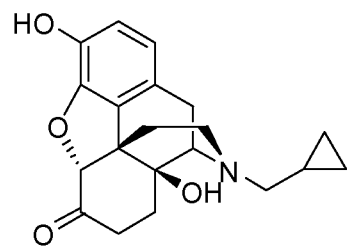
Naltrexone (4)

METHOD FOR THE N-DEMETHYLATION OF N-METHYL HETEROCYCLES

FIELD OF THE INVENTION

The present invention relates to novel methods of N-demethylating N-methyl heterocycles, particularly N-methyl alkaloids, more particularly morphine and tropane alkaloids.

BACKGROUND

Naturally occurring opiates such as morphine and codeine possess an N-methyl group. Varying this substituent produces profound pharmacological effects and there are a number of clinically relevant, semi-synthetic opiates in which the N-methyl group has been replaced by other alkyl moieties. Substituents such as allyl, cyclopropylmethyl and cyclobutylmethyl typically endow antagonist properties, though agonist activity is restored with longer alkyl groups such as phenethyl. For example, Nalorphine (1) (FIG. 1), which has an N-allyl group, has mixed agonist and antagonist activity, while N-phenethylnormorphine (2) acts as an µ agonist with 10 fold greater potency than morphine itself.[1] The combination of an N-allyl or N-cyclopropylmethyl group and some additional C-ring modifications (6-keto and 14-hydroxy functionality) affords the potent antagonists, Naloxone (3) and Naltrexone (4), respectively. N-demethylation of natural opiates is therefore a key chemical transformation in the synthesis of semi-synthetic opiates.

N-Demethylation of natural opiates has been achieved in many ways including the use of reagents such as cyanogen bromide (von Braun reaction),[2] chloroformates[3] and diethyl azodicarboxylate,[4] as well as procedures utilising photochemistry,[5] electrochemistry[6] and microorganisms.[7] It has also been shown that the $FeSO_4 \cdot 7H_2O$-mediated non-classical Polonovski reaction is also effective in the N-demethylation of several opiate alkaloids.[8] These and other methods for the N-demethylation of alkaloids have been the subject of a recent review.[9]

The $FeSO_4 \cdot 7H_2O$ reaction is described, for instance, in WO 02/16367. In that process, the tertiary N-methylamine of the N-methylated opiate is converted to the N-methyl, N-oxide by reaction with a suitable oxidising agent. The N-methyl, N-oxide is then converted to the secondary amine (ie the methyl group is removed) by reaction with a reducing agent such as $FeSO_4 \cdot 7H_2O$.

The N-demethylation step is typically problematic; requiring the use of toxic and expensive reagents and proceeds in low chemical yield.

Recently, a one-pot synthetic method for the N-demethylation of morphine and tropane alkaloids has been disclosed by Hudlicky's group in Carroll et al, *Adv. Synth. Catal.* 2008, 350, 2984-2992[10] and WO 2009/003272[11]. The method discloses the use of Pd(0), Pd(II) or Cu(II) complexes, with or without an oxidant, in various solvents in order to N-demethylate hydrocodone, codeine and tropine or to N-demethylate and N-acylate in one step. Remarkably, the technique does not rely on the preparation of the N-methyl, N-oxide. In fact, the authors of Carrol et al note that the Cu(II) catalysed procedure does not N-demethylate hydrocodone N-oxide. They state at pp 2985-2986:

Unlike the conditions reported by Scammells, which require the initial formation and isolation of the corresponding N-oxide prior to subsequent demethylation, the present process constitutes a one-pot procedure. In fact, we found that prior formation of the corresponding hydrocodone N-oxide and subsequent treatment with $Cu(OAc)_2$ and $(NH_4)_2S_2O_8$ resulted in no demethylation, suggesting that the Cu catalysed process follows a different mechanism.

In a later article (Chaudhary et al, *Collect. Czech. Chem. Commun.* 2009, 74 (7-8), 1179-1193),[12] Hudlicky and co-workers also commented on the limited scope of the above-mentioned[10,11] methodology. They state:

" . . . we had observed that palladium-catalyzed demethylations seemed to be limited to hydrocodone and a few tropane-type alkaloids".

There is a need for reagents and procedures to effect the N-demethylation of opiate alkaloids cleanly and in good yield.

SUMMARY OF THE INVENTION

The present inventors have surprisingly found that transition metals with an oxidation state of zero, including but not limited to chromium(0) and iron(0), are effective reagents for N-demethylation of opiate alkaloids. They are also effective in the N-demethylation of other alkaloids such as tropine and atropine. The method can readily be applied to other N-methyl heterocycles. The method provides N-demethylated N-methyl heterocycles cleanly and in good to excellent yields.

The present invention therefore provides a method of N-demethylating an N-methylated heterocycle, said method comprising the steps of (i) oxidising an N-methylated heterocycle to form a N-methyl, N-oxide heterocycle, and then (ii) exposing the N-methyl, N-oxide heterocycle to a transition metal with an oxidation state of zero.

In another aspect, there is provided a method of preparing a N-demethylated heterocycle from an N-methyl, N-oxide heterocycle by (i) providing a N-methyl, N-oxide heterocycle formed from a N-methylated heterocycle; and (ii) exposing the N-methyl, N-oxide heterocycle to a transition metal with an oxidation state of zero.

N-Demethylated heterocycles prepared by the methods of the present invention are also provided.

In another form of the present invention, the present inventors have found that ferrocene or a substituted derivative thereof and Cr(III) can substitute for the transition metal having an oxidation state of zero.

BRIEF DESCRIPTION OF THE FIGURES

FIG. 1 depicts four semi-synthetic opiate alkaloids.

DETAILED DESCRIPTION

The present invention provides a method of N-demethylating an N-methylated heterocycle, said method comprising the steps of (i) oxidising an N-methylated heterocycle to form the N-methyl, N-oxide heterocycle, and then (ii) exposing the N-methyl, N-oxide heterocycle to a transition metal with an oxidation state of zero.

In a preferred form, the N-methyl heterocycle is an alkaloid. Preferably, a morphine (opiate) alkaloid or a tropane alkaloid.

Preferably, the N-methyl, N-oxide is in the form of an acid salt. More preferably, the hydrochloride salt.

The prefix "nor" is often applied to the name of a naturally occurring alkaloid after it has been N-demethylated to indicate that the methyl group has been removed. For instance, morphine which has been N-demethylated may be termed normorphine.

N-methyl morphine alkaloids are alkaloids based on the morphinan ring system which is set out below as Formula I:

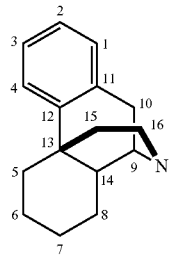

I

Examples of N-methyl morphine alkaloids which may be N-demethylated in accordance with the present invention include morphine, codeine, codeine methyl ether, ethyl morphine (dionine), dextromethorphan, oxycodeinone, thebaine, oripavine, oxymorphone, oxymorphinone, heroin, 14-hydroxy codeinone, dihydrocodone, oxycodone, pholcodeine, etorphine, dihydromorphine, oxymorphone, hydromorphone, hydrocodone, thevinone and levorphanol. The compounds may be protected where appropriate.

Morphine and codeine are naturally occurring morphine alkaloids which have a double bond at the 7 position. Thebaine and oripavine are naturally occurring morphine alkaloids which have a 6,8-diene system.

Morphine alkaloids having the 6,8-diene system are important because it is the 6,8-diene that is oxidised during the incorporation of the 14-hydroxy group in the synthesis of 14-hydroxy opiates and the diene system is involved in a Diels-Alder reaction with an appropriate dienophile in the synthesis of orvinols.

Generally speaking, the known N-demethylation techniques are not particularly effective when applied to morphine alkaloids having the 6,8-diene systems. This may be due in part to the sensitivity of the diene (see *Current Medicinal Chemistry*, 2009, 16, 3215-3242[13]). The yields of the N-demethylated product are typically moderate to low and the process unreliable.

The increasing availability of poppies which are enriched with morphine alkaloids having the 6,8-diene system means that a convenient means of demethylating such compounds would be of significant interest. The present inventors have found that, surprisingly, the method of the present invention can N-demethylate morphine alkaloids having the 6,8-diene system cleanly and in high yields (greater than 85% in some cases).

In one embodiment, therefore, the N-methyl morphine alkaloid is a N-methyl morphine alkaloid which has a 6,8-diene system. Examples include thebaine and oripavine.

Tropane alkaloids are bicyclo-[3.2.1]-azabicyclic methylamines. Particular examples include tropinone, tropane, tropine, atropine and cocaine.

It would be understood by those skilled in the art that the method of the present invention may also affect other substituents of the N-methyl heterocycle, such as hydroxy groups. Thus, it is usually desirable to first protect the hydroxy groups with a protecting group which may optionally be removed after the N-demethylation steps are completed. Protecting groups, which may be temporary or permanent, are known in the art and methods for their installation and removal are described in standard references such as *Protective Groups in Organic Synthesis*, T. W. Greene and P Wutz, John Wiley and Son, 2nd Edition (1991)[14]. Exemplary hydroxy protecting groups include $C_{1-6}$alkyl (including straight, branched and cyclic isomers of methyl, ethyl, propyl, butyl, pentyl and hexyl), aryl (eg phenyl), benzyl, acyl (eg $C(O)C_{1-6}$alkyl, wherein alkyl is as described above) and silyl groups. Preferred hydroxy protecting groups include methyl, ethyl, propyl, benzyl, and acetyl. Other groups which may also require protection are keto groups. These may be protected for example as acetals. Other suitable protecting groups for ketones are also a described in Greene and Wutz supra.

The first step (Step (i) of the method) involved in the N-demethylation of an N-methyl heterocycle is the treatment of the N-methyl compound with a suitable oxidizing agent to form the N-methyl, N-oxide. This step is well known to those in the art and they would be aware of suitable oxidants that can convert tertiary amines to the corresponding amine-N-oxides. Accordingly, in one embodiment step (i) is performed by exposing the N-methyl, N-oxide heterocycle to an oxidising agent. Exemplary oxidizing agents include hydrogen peroxide, m-chloroperbenzoic acid, peracetic acid, sodium percarbonate, and monoperoxy magnesium phthalate. Hydrogen peroxide is the most likely oxidising agent to be used in an industrial setting. In one embodiment, the oxidizing agent is selected from hydrogen peroxide and m-chloroperbenzoic acid.

Preferably the oxidising agent is added in a range of 1-5 equivalents. In one embodiment, the oxidising agent is present at about one molar equivalent. In another embodiment, the oxidising agent is present as a molar excess, for example at least about 1.2 equivalents, more preferably about 1.5-5 equivalents, yet more preferably at least about 3 equivalents. The reaction may be carried out at any suitable temperature which allows the desired oxidation to proceed, however, in order to minimise side products, about −5° C. is preferred. Ambient temperature, such as about 20-30° C. is also a preferred range in order to avoid additional costs associated with cooling or heating. The reaction is carried out for a time to achieve the desired conversion and may depend on the amount of material being treated, the amount of oxidising agent present and the temperature at which the reaction is carried out. Monitoring the reaction by a chromatographic means, such as thin layer chromatography (TLC) will allow the skilled practitioner to determine a suitable time. Suitably, the oxidation reaction is carried out for at least 30 minutes, such as at least 1 or 2 hours.

The second step in the reaction (Step (ii) of the method) involves the exposure of the N-methyl, N-oxide heterocycle to a transition metal having an oxidation state of zero.

Preferably, the transition metal is a first row transition metal. More preferably, the transition metal is selected from the group consisting of chromium (Cr) and iron (Fe). Even more preferably, the transition metal is iron.

WO 2009/003272[11] also discloses the use of iron dust as a catalyst in a one pot N-demethylation procedure. This disclosure is purely speculative as the successful use of elemental transition metals is not exemplified in the specification. The successful use of elemental metals is also not disclosed as the specification of WO 2009/003272[11] at paragraph [007] states that elemental palladium does not work. In addition, the techniques disclosed in WO 2009/003272[11] do not require the formation of the N-methyl, N-oxide prior to or during exposure to the metal.

In one embodiment, the N-methyl, N-oxide is not isolated before exposure to the transition metal having an oxidation state of zero. That is, step (i) and step (ii) are carried out in the same reaction vessel. In another embodiment, the N-methyl, N-oxide is isolated before exposure to the metal.

The transition metal can be present as the pure metal, such as iron powder. Alternatively, it may be present in the form of an alloy or composite material such as stainless steel which contains elemental chromium, iron, manganese, nickel and molybdenum. In another form, the transition metal may be galvanized iron which contains other elements including zinc. In another form, the transition metal may be part of a complex in which the metal is in a zero oxidation state such as is the case with certain carbonyl complexes and the like.

In one embodiment, the transition metal is present as the pure metal, or as part of an alloy or a composite. This allows the transition metal to be used as part of a heterogeneous reaction mixture which allows for ready removal of the transition metal after reaction.

In one preferred embodiment, the transition metal is Fe(0) in the form of the elemental metal or as part of an alloy. The alloy may be, for example, stainless steel.

In one embodiment of the present invention, the transition metal comprises from 0.05-5 equivalents of the N-methyl heterocycle.

In one embodiment, the transition metal is present in catalytic quantities, ie less than one equivalent.

Step (ii) of the method may be carried out in a suitable solvent such as acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethyl ether, diethylene glycol, diglyme (diethylene glycol dimethyl ether), 1,2-dimethoxyethane (glyme, DME), dimethylether, dimethylformamide (DMF), dimethyl sulfoxide (DMSO), dioxane, ethanol, ethyl acetate, ethylene glycol, glycerine, heptane, hexamethylphosphoramide (HMPA), hexamethylphosphorous triamide (HMPT), hexane, methanol, methyl t-butyl ether (MTBE), methylene chloride, N-methyl-2-pyrrolidinone (NMP), nitromethane, pentane, petroleum ether (ligroine), 2-propanol, pyridine, tetrahydrofuran (THF), toluene, triethyl amine, water, and xylenes, and various mixtures or combinations of these solvents.

Preferred solvents for step (ii) of the method include i-PrOH, $CHCl_3$, MeOH, ethanol and dichloromethane, and various mixtures or combinations of these solvents.

In a further embodiment, a ferric salt such as $FeCl_3 \cdot 6H_2O$ or $Fe_2(SO_4)_3 \cdot 9H_2O$ is also included in step (ii) of the method. The addition of a ferric salt has been found to improve the yield of the N-demethylated product.

The ferric salt may be present in catalytic quantities.

In a further embodiment, an inorganic salt such as $CuSO_4$, $ZnSO_4$, $CuCl_2$, $CuCl$, $Cu(NO_3)_2$, or $CO(NO_3)_2$ is also included in step (ii) of the method. The presence of alternative anions may influence the product ratio and yield by analogy with the findings in J. P. Ferris, R. D. Gerwe, G. R. Gapsi, *J. Am. Chem. Soc.* 1967, 89, 5270[15] and S. Thavaneswaran, P. J. Scammells, *Bioorg. Med. Chem. Lett.* 2006, 16, 2868[8b].

In a further embodiment, an ion-exchange resin or cellulose such as Amberlite IR-120 ($Na^+$) is also included in step (ii) of the method. These resins have been shown to greatly enhance the yield and/or rate of N-demethylation.

In a further embodiment, N-demethylation (Step (ii) of the method) is conducted under an inert atmosphere such as under nitrogen or argon.

In a further embodiment, N-demethylation (Step (ii) of the method) is conducted in air or in the presence of oxygen.

A method of preparing a N-demethylated heterocycle from an N-methyl, N-oxide heterocycle by (i) providing a N-methyl, N-oxide heterocycle formed from a N-methylated heterocycle; and (ii) exposing the N-methyl, N-oxide heterocycle to a transition metal with an oxidation state of zero.

If desired, and once the N-methyl group has been removed, an appropriate non-methyl N-substituent (R) can be introduced using methods known in the art. Accordingly the present invention provides a method of converting an N-methyl heterocycle to a non-methyl N-substituted heterocycle comprising:

demethylating said N-methyl heterocycle as described above;

treating the N-demethylated heterocycle with a compound of formula R-L, where R is a non-methyl substituent and L is a leaving group, under such conditions such that the nitrogen of the heterocycle is substituted with R.

An example of such a treatment would be treatment of the N-demethylated compound with R—Br and a base such as $NaHCO_3$ or $K_2CO_3$. Exemplary R groups include $C_{2-6}$alkyl, such as straight chain, branched and cyclic isomers of ethyl, propylbutyl, isobutyl, pentyl, (all isomers), hexyl (all isomers), cyclopropylmethyl (buprenorphine), and cyclobutylmethyl (as found in nalbuphine and butorphanol), $C_{2-6}$ alkenyl residues such as allyl (as found in nalorphine) and $C_{2-6}$ alkynyl, such as propargyl.

N-demethylated heterocycles prepared by the methods of the present invention are also provided.

In another form of the present invention, the present inventors have found that ferrocene, a substituted thereof, or Cr(III) can substitute for the transition metal having an oxidation state of zero. N-demethylations carried out using these substrates have been found to be clean and high yielding.

The substituted derivative of ferrocene may be selected from the group consisting of 1,1'-dimethylferrocene ($Me_2Fe$), decamethylferrocene ($Me_{10}Fe$) and ferroceneacetic acid (FAA) although the present invention is not limited to these substituted ferrocenes.

In order that the nature of the present invention may be more clearly understood preferred forms thereof will now be described by reference to the following non-limiting Examples.

Reactions as described in Examples 1-25 and 30 were conducted under an atmosphere of nitrogen using degassed solvents.

EXAMPLES

N-demethylation of Tertiary N-methylamines with Ferrocene

General Procedure for N-Demethylation with Ferrocene

Scheme 1

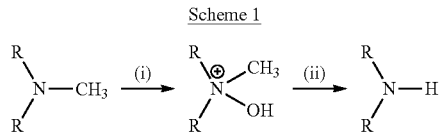

Step (i) N-oxidation of the Tertiary N-methylamine

To a stirred solution of the tertiary N-methylamine in a suitable solvent such as DCM, $CHCl_3$ or MeOH at −20° C. to −30° C. was added an oxidant such as m-CPBA or $H_2O_2$. When the reaction was complete, the N-oxide was isolated via either Method A, B or C.

Method A:

The reaction mixture was extracted with 10% NaOH to remove the m-CBA by-product. The organic layer was then washed with 1 N HCl, dried (Na$_2$SO$_4$), filtered and concentrated to afford the N-oxide hydrochloride.

Method B:

The reaction mixture was extracted with 1 N HCl (×3). The extracts were combined, washed with CHCl$_3$ (×2), and concentrated under reduced pressure to afford the desired N-methylamine N-oxide hydrochloride.

Method C:

Ice water was added to the reaction mixture and the layers separated. The pH of the aqueous layer was adjusted to 2 (6 N HCl), extracted with CHCl$_3$ (×4) and then with CHCl$_3$/i-PrOH (3:1). The latter extracts were dried, filtered and concentrated to afford the N-oxide hydrochloride.

Step (ii) N-Demethylation of the Tertiary N-methylamine N-oxide Hydrochloride with Ferrocene Method A:

A solution of the tertiary N-methylamine N-oxide hydrochloride (approx. 0.27 mmol) and ferrocene (0.1-2 mol equiv) in a solvent such as MeOH, i-PrOH or CHCl$_3$ (10 mL) was stirred at 40-70° C. until reaction was complete. The reaction mixture was concentrated to dryness to give a crude mixture of the hydrochloride salt of the N-nor compound and the starting tertiary N-methylamine. Pure N-nor compound was isolated either via column chromatography on SiO$_2$ [eluting with a gradient of CHCl$_3$/MeOH/NH$_4$OH (90:10:1-85:15:1; solvent system A) or ethyl acetate/MeOH/NH$_4$OH (70:30:1-60:40:1; solvent system B)] (Method A) or via extraction of an aqueous solution of the crude at pH 2-10 with a suitable solvent (Method B).

Method B:

N-Demethylation of the tertiary N-methylamine N-oxide hydrochloride was conducted with ferrocene as described above with 0.5-1.0 g of Amberlite IR-120 (Na$^+$) resin added. When the reaction was complete, the resin was filtered off and the filtrate was subsequently processed as described above.

Example 1

Preparation of N-Noroxycodeinone (A3)

Scheme 2

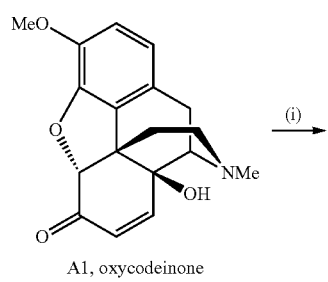

A1, oxycodeinone

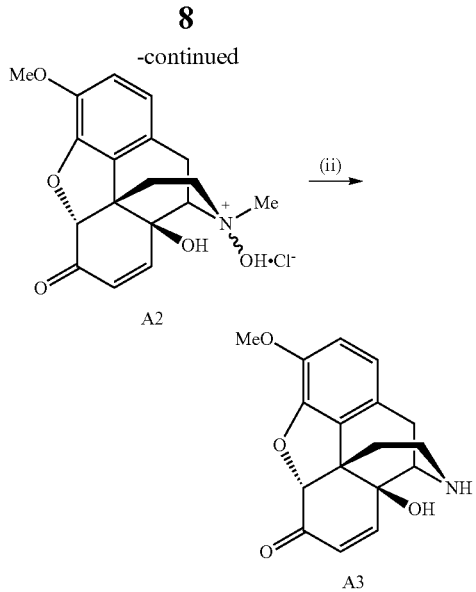

Preparation of Oxycodeinone (A1) from Thebaine

Oxycodeinone (A1) was prepared from thebaine according to published procedures.[16]

Step (i) N-Oxidation of Oxycodeinone (A1) to Oxycodeinone N-oxide Hydrochloride (A2)

Following the general procedure, m-CPBA (1.43 g of a max 77% reagent, approx. 6.38 mmol) was added to a stirred solution of A1 (1.38 g, 4.40 mmol) in CHCl$_3$ (140 mL) at −20° C. After 20 min, the solution was extracted with 1 N HCl (20 mL×3). The extracts were combined and concentrated to dryness. This provided oxycodeinone N-oxide hydrochloride (A2) as an off-white solid, 1.62 g (100%).

Step (ii) N-Demethylation of Oxycodeinone N-oxide Hydrochloride (A2) to N-noroxycodeinone (A3)

According to the general procedure, a solution of A2 (200 mg, 0.547 mmol) and ferrocene (50 mg, 0.269 mmol) in CHCl$_3$ (25 mL) was stirred at 40° C. for 5 h. The reaction mixture was concentrated to dryness, 5% aqueous HCl (30 mL) added, and the resulting solution extracted with DCM (150 mL) and CHCl$_3$ (100 mL). The solution was then heated at 50° C. for 60 min and left to cool. The pH of the solution was adjusted to 7 (conc. NH$_4$OH) and successively extracted with DCM (15 mL×2) and CHCl$_3$ (25 mL×4); these extracts were combined and concentrated to afford oxycodeinone (A1), 68 mg (40%). The pH of the aqueous layer was then adjusted to 9-10 (conc. NH$_4$OH) and extracted with CHCl$_3$/i-PrOH (3:1, 20 mL×4). The CHCl$_3$/i-PrOH extracts were combined and concentrated to dryness to afford N-noroxycodeinone (A3) as a tan solid, 82 mg (50%).

N-Demethylation of A2 was repeated using i-PrOH as solvent. Results and reaction conditions are summarized in Table 1A.

Physical data for A3: $^1$H NMR (D$_2$O/CF$_3$CO$_2$D) δ 6.93 (d, J=10.2 Hz, 1H), 6.88-6.77 (m, 2H), 6.15 (d, J 10.2 Hz, 1H), 4.94 (s, 1H), 4.01 (m, 1H), 3.74 (s, 3H), 3.29-3.12 (m, 3H), 2.92 (ddd, J 4.0, 13.5 and 13.5 Hz, 1H), 2.64 (ddd, J 5.1, 13.5 and 13.5 Hz, 1H), 1.83 (dd, J 4.0 and 13.5 Hz, 1H); $^{13}$C NMR (D$_2$O/CF$_3$CO$_2$D) δ 202.9, 147.4 143.1, 142.2, 132.7, 128.2, 122.7, 120.8, 115.2, 85.8, 66.1, 56.2, 56.1, 45.8, 36.8, 27.1, 24.8; ES-MS m/z 300 [M+H]; HRMS $C_{17}H_{18}NO_4$ calcd for [M+H]$^+$ 300.1230, found 300.1240.

Example 2

Preparation of N-Noroxymorphinone (B3)

Scheme 3

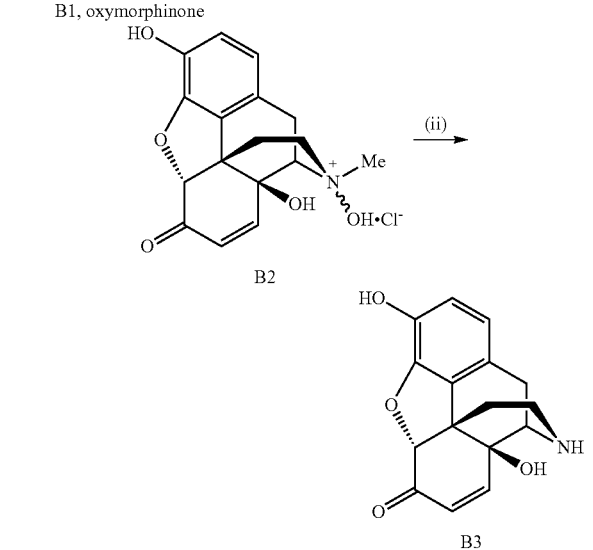

Preparation of Oxymorphinone (B1) from Oripavine

According to literature methods for the preparation of oxycodeinone from thebaine,[16] oripavine (1.00 g of 78% w/w, 2.62 mmol) was treated with two portions of m-CPBA (0.82 g in total of max 77% reagent, approx. 3.66 mmol) in HOAc (4.5 mL) and TFA (0.35 mL). When the reaction was complete, the mixture was poured into ice-water (20 mL). After stirring for 30 min, the solid was removed by filtration. The filtrate was extracted with CHCl$_3$ (5 mL×2), made basic to pH 9 with conc. NH$_4$OH, and extracted with CHCl$_3$/i-PrOH (5:1; 20 mL×4). The latter extracts were combined, dried (Na$_2$SO$_4$), filtered and concentrated to give oxymorphinone (B1) as an off-white solid, 670 mg (85%).

Step (i) N-Oxidation of Oxymorphinone (B1) to Oxymorphinone N-oxide Hydrochloride (B2)

According to the general procedure, N-oxidation of B1 (600 mg, 2.00 mmol) with m-CPBA (654 mg of a max 77% reagent, approx. 2.92 mmol) gave, following Method B workup procedure, oxymorphinone N-oxide hydrochloride (B2) as an off-white solid, 697 mg (99%).

Step (ii) N-Demethylation of Oxymorphinone N-oxide Hydrochloride (B2) to N-noroxymorphinone (B3)

According to the general procedure, B2 (100 mg, 0.284 mmol) and ferrocene (10.6 mg, 0.057 mmol) in i-PrOH (10 mL) was heated at 40° C. for 17 h. The reaction mixture was concentrated to dryness. To the residue was added 1 N HCl (30 mL) and the solution extracted with DCM (25 mL×2). The pH of the aqueous layer was adjusted to 7 (conc. NH$_4$OH) and extracted with CHCl$_3$ (40 mL×5) and then adjusted to 9 (conc. NH$_4$OH) and extracted with CHCl$_3$/i-PrOH (3:1, 25 mL×4). The CHCl$_3$ extracts at pH 7 were combined and concentrated to give oxymorphinone (B1), 27 mg (32%). The CHCl$_3$/i-PrOH (3:1) extracts were combined and concentrated to dryness to afford N-noroxymorphinone (B3) as a tan solid, 27 mg (34%); $^1$H NMR (D$_2$O/CF$_3$CO$_2$D) δ 6.95 (d, J 9.9 Hz, 1H), 6.77-6.70 (m, 2H), 6.17 (d, J 9.9 Hz, 1H), 4.94 (s, 1H), 4.01 (m, 1H), 3.30-3.12 (m, 3H), 2.93 (ddd, J 3.9, 13.2 and 13.2 Hz, 1H), 2.65 (ddd, J 5.1, 13.2 and 13.2 Hz, 1H), 1.86 (dd, J 3.9 and 14.1 Hz, 1H); $^{13}$C NMR (D$_2$O/CF$_3$CO$_2$D) δ 196.6, 147.5, 142.4, 138.4, 132.7, 128.6, 122.1, 120.9, 118.6, 85.8, 66.2, 56.2, 46.0, 36.9, 27.2, 24.8; ES-MS m/z 286 [M+H]; HRMS $C_{16}H_{16}NO_4$ calcd for [M+H]$^+$ 286.1074, found 286.1085.

Example 3

Preparation of N-Noroxycodone (C3)

Scheme 4

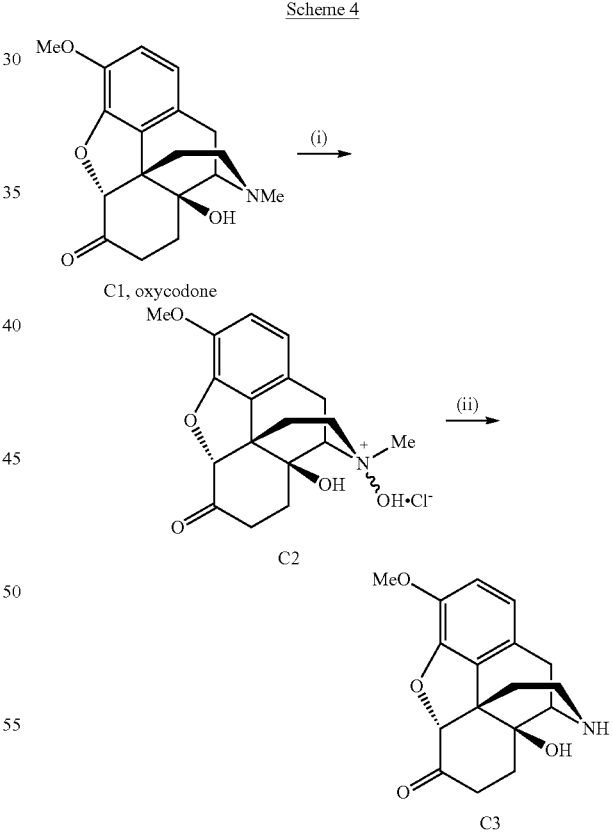

Preparation of Oxycodone (C1) from Oxycodeinone (A1)

According to literature methods,[17] catalytic hydrogenation (atmospheric H$_2$) of oxycodeinone (841 mg, 2.68 mmol) over 5% Pd—BaSO$_4$ (280 mg, 0.134 mmol of Pd) in HOAc/H$_2$O (1:9, 80 mL) for 3 days at RT provided oxycodone (C1) as an off-white solid, 830 mg (98%).

Step (i) N-Oxidation of Oxycodone (C1) to Oxycodone N-oxide Hydrochloride (C2)

According to the general procedure, N-oxidation of C1 (463 mg, 1.47 mmol) with m-CPBA (477 mg of a max 77% reagent, approx. 2.13 mmol) in CHCl$_3$ (50 mL) gave, after workup according to Method B, oxycodone N-oxide hydrochloride (C2) as a colourless foam, 535 mg (98%).

Step (ii) N-Demethylation of Oxycodone N-oxide Hydrochloride (C2) to N-noroxycodone (C3)

According to the general procedure, a stirred suspension of C2 (100 mg, 0.272 mmol), ferrocene (100 mg, 0.538 mmol), Amberlite IR-120 (Na$^+$) (1 g) and i-PrOH (10 mL) was heated at 60° C. for 2 h. The reaction mixture was filtered and the filtrate was concentrated to dryness. Subsequent workup was according to Method A. The first fraction gave oxycodone (C1) (16 mg, 19%) and the second fraction gave N-noroxycodone (C3) as a tan solid, 48 mg (59%).

The above reaction was repeated without the addition of resin. When the reaction was complete, the mixture was concentrated to dryness, 10% aqueous HCl was added to the remaining residue and the resulting solution was heated at 50° C. for 24 h and left to cool. Subsequent isolation of the N-nor compound C3 was according to workup Method B. Results are summarized in Table 1A.

Physical data for C3: $^1$H NMR (D$_2$O/CF$_3$CO$_2$D) δ 6.88-6.75 (m, 2H), 4.92 (s, 1H), 3.75 (br s, 4H), 3.24-3.05 (m, 3H), 2.90 (ddd, J 5.1, 15.0 and 15.0 Hz, 1H), 2.75 (ddd, J 3.6, 13.2 and 13.2 Hz, 1H), 2.56 (ddd, J 4.8, 13.5 and 13.5 Hz, 1H), 2.20 (m, 1H), 1.94 (m, 1H), 1.63-1.53 (m, 2H); for the hydrochloride of C3: $^{13}$C NMR (CDCl$_3$, 150.8 MHz) δ 208.5, 145.0, 143.0, 129.5, 125.2, 119.3, 114.8, 90.5, 70.2, 57.4, 56.8, 51.1, 37.2, 36.2, 32.9, 31.5, 30.1; ES-MS m/z 302 [M+H]; HRMS C$_{17}$H$_{20}$NO$_4$ calcd for [M+H]$^+$ 302.1387, found 302.1396.

Example 4

Preparation of N-Noroxymorphone (D3)

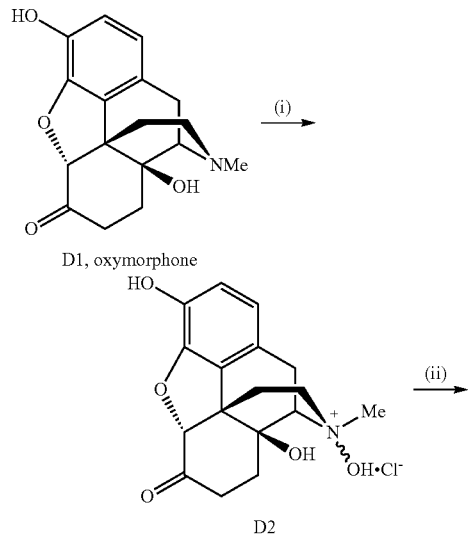

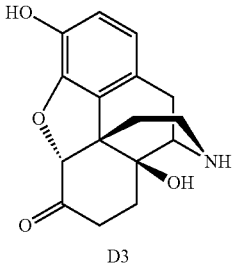

Preparation of Oxymorphone (D1) from Oxymorphinone (B1)

A solution of oxymorphinone (B1) (1.56 g, 5.21 mmol) in 10% aqueous AcOH (160 mL) was hydrogenated (atmospheric H$_2$) over 5% Pd—BaSO$_4$ (543 mg, 0.259 mmol of Pd) for 3 days at RT. The mixture was filtered through celite and the filter pad was washed with water. The filtrate and the washings were combined, made basic to pH 9 with conc. NH$_4$OH, and extracted with CHCl$_3$/i-PrOH (3:1; 50 mL×5). The extracts were combined, dried (Na$_2$SO$_4$), filtered and concentrated to give oxymorphone (D1) as a light brown solid, 1.54 g (98%).

Step (i) N-Oxidation of Oxymophone (D1) to Oxymorphone N-oxide Hydrochloride (D2)

According to the general procedure, N-oxidation of a solution of oxymorphone (D1) (0.80 g, 2.65 mmol) in CHCl$_3$ (80 mL) at −30° C. with m-CPBA (0.87 g of a max. 77% reagent, approx. 3.88 mmol) for 20 min gave, after workup according to Method B, oxymorphone N-oxide hydrochloride (D2) as a tan solid, 0.92 g (98%).

Step (ii) N-Demethylation of Oxymorphone N-oxide Hydrochloride to N-noroxymorphone (D3)

According to the general procedure, a solution of oxymorphone N-oxide hydrochloride (D2) (100 mg, 0.283 mmol) and ferrocene (10.5 mg, 0.056 mmol) in i-PrOH (10 mL) was heated at 40° C. for 48 h. The reaction mixture was concentrated to dryness. To the residue was added 1N HCl (30 mL) and the solution extracted with DCM (20 mL×2). The pH of the aqueous layer was adjusted to 7 (conc. NH$_4$OH) and extracted with CHCl$_3$ (20 mL×3) and then adjusted to 9 (conc. NH$_4$OH), saturated with NaCl, and extracted with CHCl$_3$/i-PrOH (3:1, 25 mL×5). The CHCl$_3$ extracts were combined and concentrated to afford oxymorphone (D1), 28 mg (32%). The CHCl$_3$/i-PrOH (3:1) extracts were combined and concentrated to dryness to afford N-noroxymorphone (D3) as a tan solid, 48 mg (59%); $^1$H NMR (D$_2$O/CF$_3$CO$_2$D) δ 6.64-6.56 (m, 2H), 4.80 (s, 1H), 3.67 (dd, J 2.1 and 4.8 Hz, 1H), 3.08-2.98 (m, 3H), 2.79 (ddd, J 5.1, 14.7 and 14.7 Hz, 1H), 2.66 (ddd, J 3.9, 13.2 and 13.2 Hz, 1H), 2.45 (ddd, J 5.1, 13.2 and 13.2 Hz, 1H), 2.10 (m, 1H), 1.83 (ddd, J 2.7, 4.8 and 14.1 Hz), 1.52 (dd, J 3.3 and 14.1 Hz, 1H), 1.47 (dd, J 3.9 and 14.7 Hz, 1H); $^{13}$C NMR (D$_2$O/CF$_3$CO$_2$D) δ 211.7, 143.0, 138.6, 127.3, 122.0, 120.9, 118.5, 89.3, 69.4, 57.4, 49.2, 36.7, 34.4, 30.3, 27.5, 25.7; ES-MS m/z 288 [M+H]; HRMS C$_{16}$H$_{18}$NO$_4$ calcd for [M+H]$^+$ 288.1230, found 288.1226.

Example 5

Preparation of N-Norcodeine Methyl Ether (E3)

Scheme 6

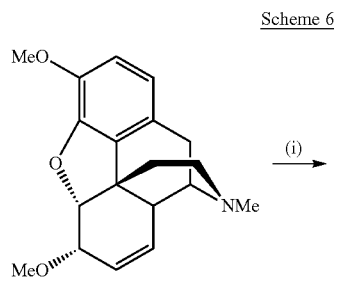

According to published procedures,[18] codeine methyl ether (E1) was reacted with m-CPBA followed by treatment with HCl to give the N-oxide hydrochloride E2. This N-oxide hydrochloride, as per general conditions, was then treated with ferrocene using either $CHCl_3$ or i-PrOH as solvent. Results are summarized in Table 1A. Physical data for E3 are consistent with the literature.[18]

Example 6

Preparation of N-Northebaine (F3)

Scheme 7

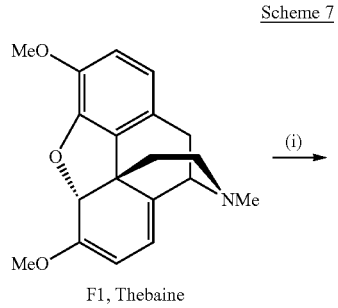

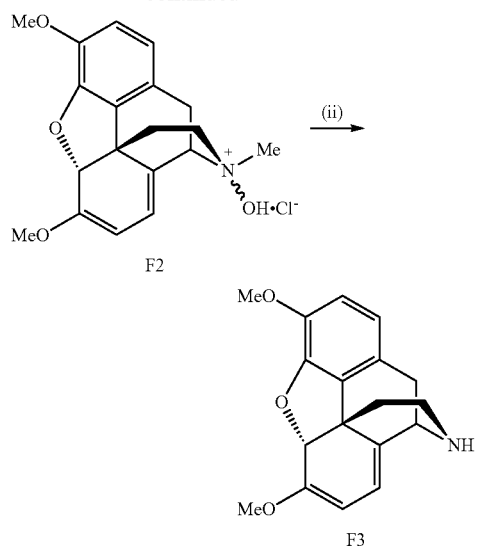

According to published procedures,[18] N-oxidation of thebaine (F1) with m-CPBA followed by treatment with HCl gave the N-oxide hydrochloride F2. This N-oxide hydrochloride was then treated with ferrocene, as per general procedure Step (ii). Results are summarized in Table 1A. Physical data for F3 are consistent with the literature.[18]

Example 7

Preparation of N-Nororipavine (G3)

Scheme 8

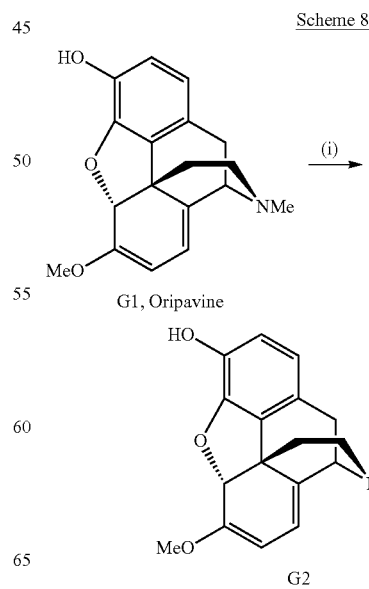

-continued

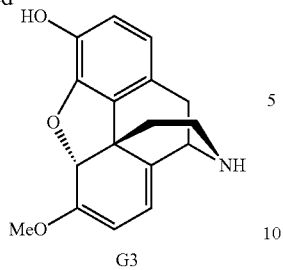

G3

-continued

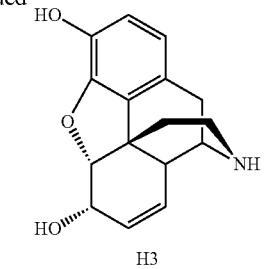

H3

According to the general procedure, oripavine (G1) and m-CPBA gave, after workup according to Method C, oripavine N-oxide hydrochloride (G2) as a tan solid in 92% yield. The N-oxide hydrochloride G2 was then respectively treated with ferrocene, with or without Amberlite IR-120 (Na$^+$) resin, as per general procedure Step (ii) Methods A/B using workup Method A, employing CHCl$_3$/MeOH as eluant. Results are summarized in Table 1A.

Physical data for the hydrochloride salt of G3: $^1$H NMR (CDCl$_3$) δ 6.69-6.56 (m, 2H), 5.51 (d, J 6.6 Hz, 1H), 5.27 (s, 1H), 5.07 (d, J 6.6 Hz, 1H), 3.96 (m, 1H), 3.63 (s, 3H), 3.25̃2.95 (m, 4H), 2.30 (br, 3H), 2.10 (ddd, J 5.1, 12.6 and 12.6 Hz, 1H), 1.86 (m, 1H); $^{13}$C NMR (CD$_3$OD) δ 155.7, 145.2, 141.6, 133.5, 127.7, 125.0, 121.2, 118.5, 117.5, 96.6, 89.2, 55.9, 55.1, 46.7, 38.8, 36.5, 35.4; ES-MS m/z 284 [M+H]; HRMS C$_{17}$H$_{18}$NO$_3$ calcd for [M+H]$^+$ 284.1281, found 284.1287.

Example 8

Preparation of N-Normorphine (H3)

Scheme 9

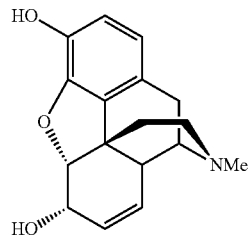

H1, Morphine

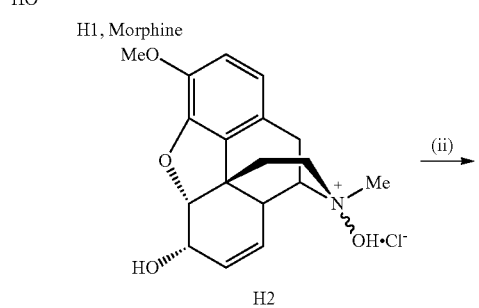

H2

Step (i) N-Oxidation of Morphine (H1) to Morphine N-oxide Hydrochloride (H2)

According to the general procedure, N-oxidation of H1 (1.98 g, 6.93 mmol) with m-CPBA (2.25 g of a max 77% reagent, approx. 10.05 mmol) in CHCl$_3$ (200 mL) and MeOH (2 mL) gave, after workup according to Method B, morphine N-oxide hydrochloride monohydrate (H2) as an off-white solid, 2.50 g.

Step (ii) N-Demethylation of Morphine N-oxide Hydrochloride (H2) to N-normorphine (H3)

A stirred solution of the N-oxide H2 (100 mg, 0.281 mmol) and ferrocene (10.5 mg, 0.05 mmol) in i-PrOH (10 mL) was heated at 40° C. for 5 days. The reaction mixture was concentrated to dryness. To the residue was added 10% aqueous HCl (30 mL) and the resulting solution extracted with CHCl$_3$ (10 mL×2). The pH of the aqueous layer was adjusted to 8 (conc. NH$_4$OH) and extracted with CHCl$_3$/i-PrOH (6:1, 20 mL×8). These extracts were combined and concentrated to give morphine, 28 mg (35%). The aqueous layer was then evaporated to dryness and the residue extracted with CHCl$_3$/i-PrOH (3:1; 20 mL×5), the extracts combined and concentrated to give N-normorphine (H3) as an off-white solid, 56 mg (62%).

Physical data for H3: $^1$H NMR (D$_2$O/CF$_3$CO$_2$D) δ 6.70-6.58 (m, 2H), 5.66 (d, J 9.6 Hz, 1H), 5.29 (d, J 9.6 Hz, 1H), 4.96 (d, J 5.7 Hz, 1H), 4.34-4.20 (m, 2H), 3.28 (m, 1H), 3.13̃2.78 (m, 4H), 2.19 (ddd, J 4.2, 13.2 and 13.2 Hz, 1H), 2.05 (m, 1H); $^{13}$C NMR of the hydrochloride salt (D$_2$O/CF$_3$CO$_2$D) δ 145.5, 137.8, 133.0, 129.3, 125.7, 123.5, 118.0, 117.5, 90.7, 65.6, 51.5, 42.1, 37.1, 36.7, 31.6, 25.7; ES-MS m/z 272 [M+H]; HRMS C$_{16}$H$_{17}$NO$_3$ calcd for [M+H]$^+$ 272.1281, found 272.1286.

Example 9

Preparation of N-Nordextromethorphan (J3)

Scheme 10

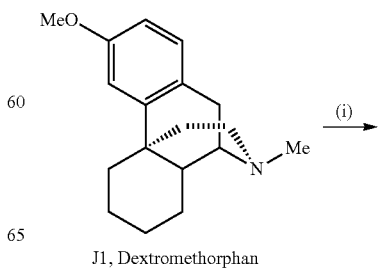

J1, Dextromethorphan

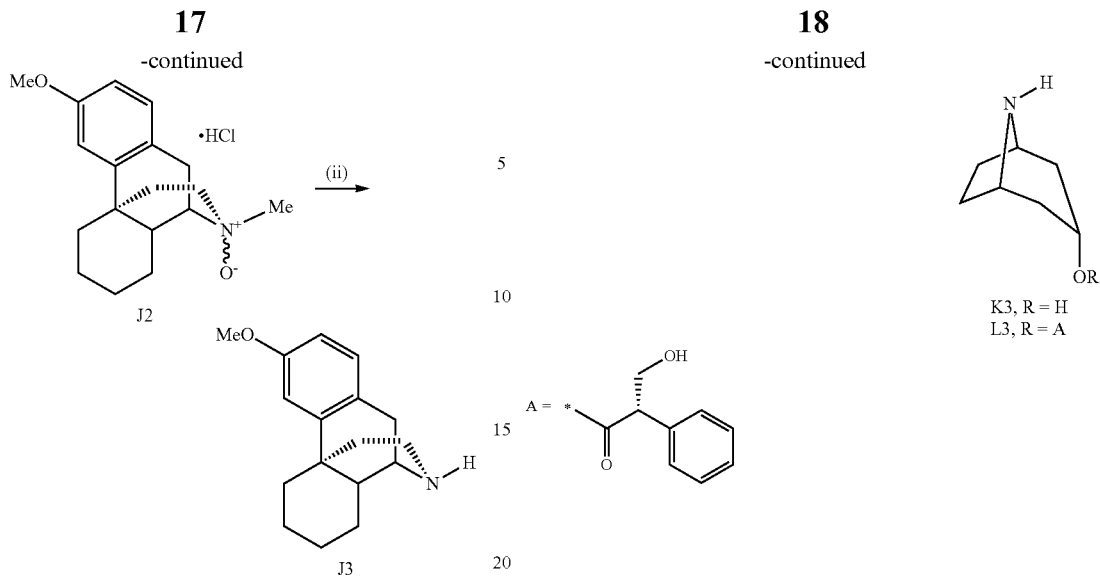

According to the general procedure Step (i), N-oxidation of dextromethorphan (J1) (2.20 g, 8.10 mmol) with m-CPBA gave, after workup Method A, dextromethorphan N-oxide hydrochloride (J2) as a colorless solid, 2.49 g (94%).

As per general procedure Step (ii), the N-oxide J2 and ferrocene in i-PrOH gave, after workup according to Method A, N-nordextromethorphan (J3) as a colorless oil. N-Demethylation of J2 was repeated replacing i-PrOH with CHCl$_3$. Results are summarized in Table 1A. Physical data for J3 are consistent with the literature.[18]

Examples 10-11A

Preparation of N-Nortropine (K3) and N-Noratropine (L3)

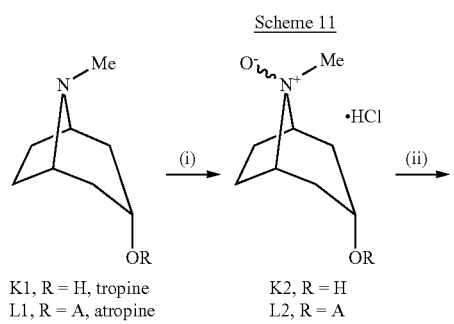

Step (i) Preparation of the N-oxide Hydrochlorides of Tropine (K2) and Atropine (L2)

According to processes described in general procedure Part (i), N-oxidation using m-CPBA, employing workup Method B: tropine monohydrate (K1) (1.00 g, 6.28 mmol) gave tropine N-oxide hydrochloride monohydrate (K2) as a colorless solid (1.32 g, 99%); atropine monohydrate (L2) (429 mg, 0.72 mmol) gave atropine N-oxide hydrochloride hydrate as colorless oil (485 mg, 95%).

Step (ii) Preparation of N-Nortropine (K3) and N-Noratropine (L3)

According to general procedure Step (ii) Method A using workup Method A: K2 gave N-nortropine (K3), and L2 gave N-noratropine (L3). Reaction conditions and yields are given in Table 1A.

N-nortropine (K3).

$^1$H NMR (D$_2$O) δ 4.11 (m, 1H), 4.00 (m, 1H), 2.39-2.30 (m, 2H), 2.20 (m, 1H), 2.14 (m, 1H), 2.08-1.90 (m, 4H); $^{13}$C NMR of the hydrochloride salt (D$_2$O) δ 62.1, 61.9, 54.1, 54.0, 35.1, 25.5; ES-MS m/z 128 [M+H]; HRMS C$_7$H$_{13}$NO calcd for [M+H]$^+$ 128.1070, found 128.1065.

N-noratropine (L3).

$^1$H NMR (D$_2$O) δ 7.57-7.40 (m, 5H), 5.02 (t, J 4.2, 1H), 4.28 (dd, J 10.2 and 12.9, 1H), 4.08-3.99 (m, 2H), 3.63 (m, 1H), 3.54 (m, 1H), 2.19-1.51 (m, 8H); $^{13}$C NMR (CDCl$_3$) δ 172.3, 135.8, 128.8, 128.1, 127.7, 68.6, 63.9, 54.5, 53.1, 53.0, 37.0, 36.7, 28.8, 28.4; ES-MS m/z 276 [M+H]; HRMS C$_{16}$H$_{22}$NO$_3$ calcd for [M+H]$^+$ 276.1594, found 276.1604.

TABLE 1A

Summary of N-Demethylation Reactions of Tertiary N-Methylamines with Ferrocene

| N-oxide•HCl (mmol) | Ferrocene (equiv) | Other additives | Solvent | Temp (° C.) | Time (h) | Yield of 3° amine | Yield of 2° amine |
|---|---|---|---|---|---|---|---|
| A2 (0.547) | 0.5 | | CHCl$_3$ | 40 | 5 | (A1) 40%$^a$ | (A3) 50%$^a$ |
| A2 (0.137) | 0.2 | | i-PrOH | 40 | 16 | (A1) 30%$^a$ | (A3) 51%$^a$ |
| B2 (0.284) | 0.2 | | i-PrOH | 40 | 17 | (B1) 32%$^a$ | (B3) 34%$^a$ |

TABLE 1A-continued

Summary of N-Demethylation Reactions of Tertiary N-Methylamines with Ferrocene

| N-oxide•HCl (mmol) | Ferrocene (equiv) | Other additives | Solvent | Temp (°C.) | Time (h) | Yield of 3° amine | Yield of 2° amine |
|---|---|---|---|---|---|---|---|
| C2 (0.272) | 2.0 | Amberlite IR-120 (Na$^+$) | i-PrOH | 60 | 2 | (C1) 19%$^b$ | (C3) 59%$^b$ |
| C2 (0.136) | 0.2 | | i-PrOH | 40 | 20 | (C1) 23%$^a$ | (C3) 58%$^a$ |
| D3 (0.283) | 0.2 | | i-PrOH | 40 | 48 | (D1) 32%$^a$ | (D3) 59%$^a$ |
| E2 (0.273) | 0.25 | | CHCl$_3$ | 50 | 22 | (E1) 7%$^b$ | (E3) 92%$^b$ |
| E2 (0.273) | 0.25 | | i-PrOH | 50 | 48 | (E1) 13%$^a$ | (E3) 75%$^a$ |
| F2 (0.253) | 0.5 | | CHCl$_3$ | 50 | 48 | (F1) 7%$^b$ | (F3) 84%$^b$ |
| G2 (0.286) | 2 | | i-PrOH | 70 | 24 | (G1) 29%$^{b,d}$ | (G3) 38%$^{b,d}$ |
| G2 (0.143) | 2 | Amberlite IR-120 (Na$^+$) | i-PrOH | 70 | 24 | (G1) 30%$^{b,d}$ | (G3) 68%$^{b,d}$ |
| H2 (0.281) | 0.2 | | i-PrOH | 40 | 120 | (H1) 35%$^a$ | (H3) 63%$^a$ |
| J2 (0.154) | 0.25 | | i-PrOH | 40 | 96 | (J1) 26%$^b$ | (J3) 70%$^b$ |
| J2 (0.309) | 0.25 | | CHCl$_3$ | 60 | 16 | (J1) 7%$^b$ | (J3) 92%$^b$ |
| K2 (0.472) | 0.2 | | i-PrOH | 80 | 24 | (K1) 46%$^c$ | (K3) 50%$^c$ |
| L2 (0.150) | 0.1 | | i-PrOH | 80 | 24 | (L1) 21%$^b$ | (L3) 59%$^b$ |

$^a$General procedure Step (ii), workup Method B.
$^b$General procedure Step (ii), workup Method A (Solvent system A).
$^c$General procedure Step (ii), workup Method A (Solvent system B).
$^d$For the column purification, no NH$_4$OH was added to the eluant; accordingly, G1 and G3 were isolated as the corresponding hydrochloride.

Example 11B

N-Demethylation Reactions of Tertiary N-Methylamines with Substituted Ferrocenes Reactions as described in Examples 1-11A were repeated replacing ferrocene with a substituted ferrocene. Examples of substituted ferrocenes include, but are not limited to, 1,1'-dimethylferrocene (Me$_2$Fe), decamethylferrocene (Me$_{10}$Fe) and ferroceneacetic acid (FAA). Results for dextromethorphan N-oxide hydrochloride (J2), dextromethorphan N-oxide (J4) or dextromethorphan N-oxide acetic acid salt (J5) are summarized in Table 1B.

N-Demethylation reactions on other representative substrates using a substituted ferrocene are summarized in Table 1C.

TABLE 1B

Summary of N-Demethylation Reactions of Dextromethorphan N-oxide hydrochloride (J2) with a Substituted Ferrocene

| Entry | Catalyst (equiv) | Solvent$^a$ | Temp (°C.) | Time (h) | % Yield$^b$ 2° amine | 3° amine |
|---|---|---|---|---|---|---|
| 1 | Me$_2$Fe (0.25) | i-PrOH | 40 | 30 | 73 | 24 |
| 2 | Me$_2$Fe (0.25) | CHCl$_3$ | 40 | 48 | 86 | 12 |
| 3 | Me$_{10}$Fe (0.25) | i-PrOH | 40 | 120 | 71 | 26 |
| 4 | FAA (0.25) | i-PrOH | 50 | 1 | 76 | 23 |
| 5 | FAA (0.25) | CHCl$_3$ | 50 | 1 | 84 | 15 |
| 6 | FAA (0.25) | i-PrOH | RT | 6 | 81 | 17 |
| 7 | FAA (0.25) | CHCl$_3$ | RT | 4 | 85 | 15 |
| 8$^c$ | FAA (0.25) | i-PrOH | 50 | 16 | 28 | 35 |
| 9$^c$ | FAA (0.25) | CHCl$_3$ | 50 | 16 | 25 | 36 |
| 10$^d$ | Me$_2$Fe (0.25) | i-PrOH | 50 | 96 | 73 | 21 |
| 11$^d$ | Me$_{10}$Fe (0.25) | i-PrOH | 50 | 30 | 69 | 25 |
| 12$^d$ | FAA (0.25) | CHCl$_3$ | 50 | 16 | 82 | 15 |

$^a$Concentration: 10 mL per 100 mg of N-oxide.
$^b$Yield obtained after column chromatography.
$^c$N-oxide free base (J4) rather than the hydrochloride salt (J2) was used.
$^d$N-oxide acetic acid salt (J5) rather the hydrochloride salt was used.

TABLE 1C

Summary of N-Demethylation Reactions of other Substrates with a Substituted Ferrocene

| Entry | N-oxide•HCl of | Catalyst (equiv) | Solvent[a] | Temp (°C.) | Time (h) | % Yield[b] 2° amine | 3° amine |
|---|---|---|---|---|---|---|---|
| 1 | Oxycodone (C2) | Me₂Fe (0.25) | CHCl₃ | RT | 22 | 35 | 29 |
| 2 | Thebaine (F2) | FAA (0.5) | i-PrOH | 40 | 24 | 58 | 18 |
| 3 | Thebaine (F2) | FAA (0.5) | CHCl₃ | RT | 16 | 53 | 25 |
| 4 | Thevinone | FAA (0.25) | CHCl₃ | RT | 2.5 | 56 | 43 |

[a]Concentration: 10 mL per 100 mg of N-oxide.
[b]Yield obtained after column chromatography.

N-demethylation of Tertiary N-methylamines Using Steel

General Procedure for N-Demethylation with Steel

Scheme 12

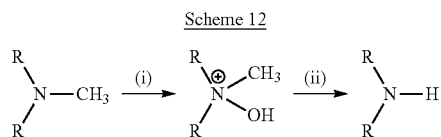

Step (i) N-Oxidation of tertiary N-methylamine

To a stirred solution of the tertiary N-methylamine in a suitable solvent such as DCM, CHCl₃ or MeOH at −20° C. to −30° C. was added an oxidant such as m-CPBA or H₂O₂. When the reaction was complete, the N-oxide was isolated via either Method A, B or C.

Method A.

The reaction mixture was extracted with 10% NaOH to remove the m-CBA by-product. The organic layer was then washed with 1 N HCl, dried (Na₂SO₄), filtered, and concentrated to afford the N-oxide hydrochloride.

Method B.

The reaction mixture was extracted with 1 N HCl (×3). The extracts were combined, washed with CHCl₃ (×2) and concentrated to afford the desired N-methylamine N-oxide hydrochloride.

Method C:

Ice water was added to the reaction mixture and the layers separated. The pH of the aqueous layer was adjusted to 2 (6 N HCl), extracted with CHCl₃ (×4) and then with CHCl₃/i-PrOH (3:1). The latter extracts were dried, filtered and concentrated to afford the N-oxide hydrochloride.

Step (ii) N-Demethylation of the Tertiary N-methylamine N-oxide Hydrochloride with Steel Method A:

To a stirred solution of the tertiary N-methylamine N-oxide hydrochloride (0.27 mmol) in a solvent such as MeOH, EtOH, i-PrOH or CHCl₃ (10 mL) was added a piece of steel (1.18 g). The mixture was heated at 40-70° C. until reaction was complete. The piece of steel was retrieved from the reaction mixture, and the reaction mixture was concentrated to dryness to give a crude mixture of the N-nor compound and the starting tertiary N-methylamine. Pure N-nor compound was isolated either via column chromatography on SiO₂ [eluting with a gradient of CHCl₃/MeOH/NH₄OH (90:10:1-85:15:1; solvent system A) or with ethyl acetate/MeOH/NH₄OH (60:40:1; solvent system B)] (workup Method A) or via extraction of an aqueous solution of the crude at different pH's with a suitable solvent (workup Method B). For example, after removal of the volatiles, 5% HCl (approx. 30 mL for 0.27 mmol) was added to the crude reaction mixture. The pH of the solution was adjusted to 7 (conc. NH₄OH) and the solution was extracted with CHCl₃ (20 mL×3) and then with CHCl₃/MeOH (19:1, 10 mL×3). These extracts were combined and concentrated to afford the starting tertiary N-methylamine. The pH of the aqueous layer was then adjusted to 9-10 using conc. NH₄OH and the solution extracted with CHCl₃ or CHCl₃/i-PrOH (3:1). These extracts, after concentration, afforded the N-nor compound.

Method B:

N-Demethylation of the opiate N-oxide hydrochloride was conducted with steel as described above with the addition of 0.5-1.0 g of Amberlite IR-120 (Na⁺) resin. When the reaction was complete, the piece of steel was retrieved from the reaction mixture; the resin was filtered off and the filtrate was subsequently processed as described above.

Examples of Steel Used

| Steel sample | % Composition |  |  |  |  |  |  |
|---|---|---|---|---|---|---|---|
|  | Cr | Ni | Cu | Zn | Mo | Sn | Fe |
| A | 0.01 |  |  | 1.47 |  |  | balance |
| B | 0.02 | 0.53 | 0.22 | 0.46 |  |  | balance |
| C | 0.05 | 0.83 | 1.17 |  | 0.01 | 0.01 | balance |

Examples 12-15

N-Demethylation of Oxycodeinone, Oxymorphinone, Oxycodone and Oxymorphone with Steel Scheme 13

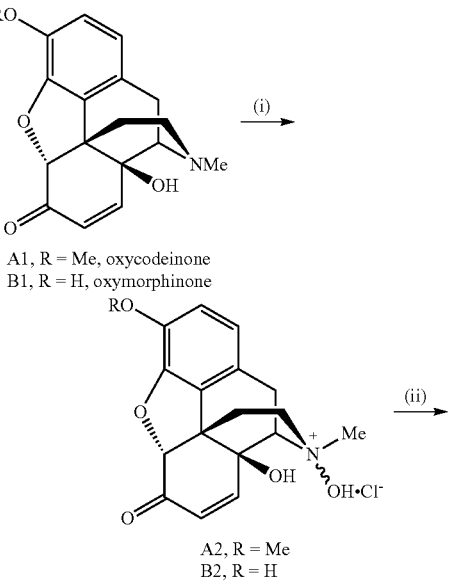

A1, R = Me, oxycodeinone
B1, R = H, oxymorphinone

A2, R = Me
B2, R = H

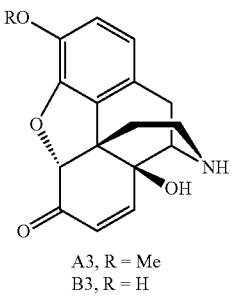

A3, R = Me
B3, R = H

Scheme 14

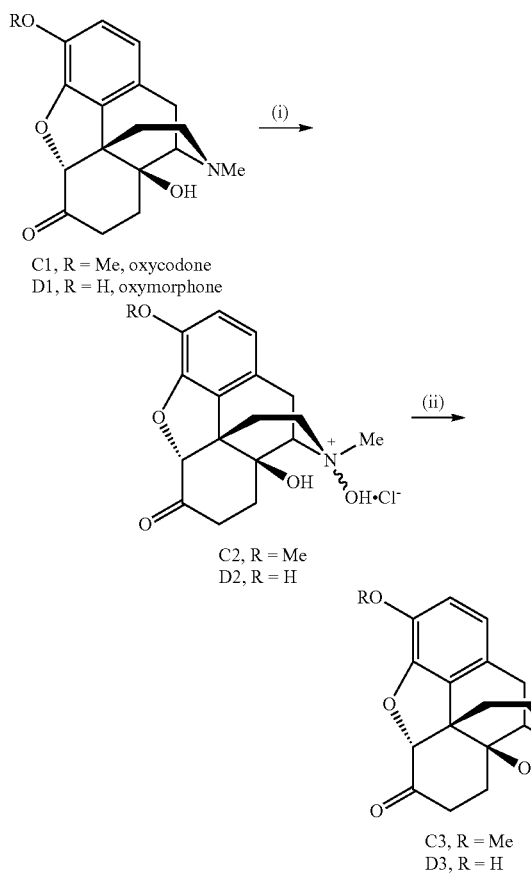

C1, R = Me, oxycodone
D1, R = H, oxymorphone

C2, R = Me
D2, R = H

C3, R = Me
D3, R = H

Preparation of Oxycodeinone (A1), Oxymorphinone (B1), Oxycodone (C1) and Oxymorphone (D1)

Oxycodeinone (A1) was prepared from thebaine according to literature[16] procedures; subsequent reduction of A1 under catalytic hydrogenation conditions[17] afforded oxycodone (C1).

Employing similar conditions used for the preparation of A1 from thebaine,[16] oxymorphinone (B1) was prepared from oripavine: thus, oripavine (1.00 g of 78% w/w, 2.62 mmol) was treated with two portions of m-CPBA (0.82 g in total of a max 77% reagent, approx. 3.66 mmol) in HOAc (4.5 mL) and TFA (0.35 mL). When the reaction was complete, the mixture was poured into ice-water (20 mL). After stirring for 30 min, the solid was removed by filtration. The filtrate was extracted with CHCl$_3$ (5 mL×2), made basic to pH 9 with conc. NH$_4$OH, and extracted with CHCl$_3$/i-PrOH (5:1; 20 mL×4). The CHCl$_3$/i-PrOH extracts were combined, dried (Na$_2$SO$_4$), filtered and concentrated to give B1 as an off-white solid, 0.67 g (85%).

A solution of B1 (1.56 g, 5.21 mmol) in 10% aqueous AcOH (160 mL) was hydrogenated (atmospheric H$_2$) over 5% Pd—BaSO$_4$ (543 mg, 0.259 mmol of Pd) for 3 days at RT. The mixture was filtered through celite and the filter pad was washed with water. The filtrate and the washings were combined, made basic to pH 9 with conc. NH$_4$OH and extracted with CHCl$_3$/i-PrOH (3:1; 50 mL×5). The extracts were combined, dried (Na$_2$SO$_4$), filtered and concentrated to give oxymorphone (D1) as a light brown solid 1.54 g (98%).

Step (i) Preparation of the N-oxide Hydrochloride of Oxycodeinone (A2), Oxymorphinone (B2), Oxycodone (C2) and Oxymorphone (D2)

According to the general procedure Part (i) using workup Method B: N-oxidation employing m-CPBA of oxycodeinone (A1) (1.38 g, 4.40 mmol) gave oxycodeinone N-oxide hydrochloride (A2) as an off-white solid, 1.62 g (100%); oxymorphinone (B1) (600 mg, 2.00 mmol) gave oxycodone N-oxide hydrochloride (B2) as a colorless foam, 697 mg (99%); oxycodone (C1) (463 mg, 1.47 mmol) gave oxycodone N-oxide hydrochloride (C2) as an off-white solid, 535 mg (98%); oxymorphone (D1) (0.80 g, 2.65 mmol) gave oxymorphone N-oxide hydrochloride (D2) as a tan solid, 0.92 g (98%).

Step (ii) Preparation of N-noroxycodeinone (A3), N-noroxymorphinone (B3), N-noroxycodone (C3) and N-noroxymorphone (D3)

According to the general procedure Part (ii), using workup Method B: A2 gave N-noroxycodeinone (A3), B2 gave N-noroxymorphinone (B3), C2 gave N-noroxycodone (C3), and D2 gave N-noroxymorphone (D3). Reaction conditions and yields are summarized in Table 2. Physical characterization data for A3, B3, C3 and D3 are as follows;

N-noroxycodeinone (A3).

$^1$H NMR (D$_2$O/CF$_3$CO$_2$D) δ 6.93 (d, J 10.2 Hz, 1H), 6.88-6.77 (m, 2H), 6.15 (d, J 10.2 Hz, 1H), 4.94 (s, 1H), 4.01 (m, 1H), 3.74 (s, 3H), 3.29-3.12 (m, 3H), 2.92 (ddd, J 4.0, 13.5 and 13.5 Hz, 1H), 2.64 (ddd, J 5.1, 13.5 and 13.5 Hz, 1H), 1.83 (dd, J 4.0 and 13.5 Hz, 1H). $^{13}$C NMR (D$_2$O/CF$_3$CO$_2$D) δ 202.9, 147.4 143.1, 142.2, 132.7, 128.2, 122.7, 120.8, 115.2, 85.8, 66.1, 56.2, 56.1, 45.8, 36.8, 27.1, 24.8; ES-MS m/z 300 [M+H]; HRMS C$_{17}$H$_{18}$NO$_4$ calcd for [M+H]$^+$ 300.1230, found 300.1240.

N-Noroxymorphinone (B3).

$^1$H NMR (D$_2$O/CF$_3$CO$_2$D) δ 6.95 (d, J 9.9 Hz, 1H), 6.77-6.70 (m, 2H), 6.17 (d, J 9.9 Hz, 1H), 4.94 (s, 1H), 4.01 (m, 1H), 3.30-3.12 (m, 3H), 2.93 (ddd, J 3.9, 13.2 and 13.2 Hz, 1H), 2.65 (ddd, J 5.1, 13.2 and 13.2 Hz, 1H), 1.86 (dd, J 3.9 and 14.1 Hz, 1H). $^{13}$C NMR (D$_2$O/CF$_3$CO$_2$D) δ 196.6, 147.5, 142.4, 138.4, 132.7, 128.6, 122.1, 120.9, 118.6, 85.8, 66.2, 56.2, 46.0, 36.9, 27.2, 24.8; ES-MS m/z 286 [M+H]; HRMS C$_{16}$H$_{16}$NO$_4$ calcd for [M+H]$^+$ 286.1074, found 286.1085.

N-Noroxycodone (C3).

$^1$H NMR (CDCl$_3$) δ 6.88-6.75 (m, 2H), 4.92 (s, 1H), 3.75 (br s, 4H), 3.24-3.05 (m, 3H), 2.90 (ddd, J 5.1, 15.0 and 15.0 Hz, 1H), 2.75 (ddd, J 3.6, 13.2 and 13.2 Hz, 1H), 2.56 (ddd, J 4.8, 13.5 and 13.5 Hz, 1H), 2.20 (m, 1H), 1.94 (m, 1H), 1.63-1.53 (m, 2H). $^{13}$C NMR for the hydrochloride salt of C3 (CDCl$_3$) δ 208.5, 145.0, 143.0, 129.5, 125.2, 119.3, 114.8, 90.5, 70.2, 57.4, 56.8, 51.1, 37.2, 36.2, 32.9, 31.5, 30.1. ES-MS m/z 302 [M+H]; HRMS C$_{17}$H$_{20}$NO$_4$ calcd for [M+H]$^+$ 302.1387, found 302.1396.

N-Noroxymorphone (D3).

$^1$H NMR (D$_2$O/CF$_3$CO$_2$D) δ 6.64-6.56 (m, 2H), 4.80 (s, 1H), 3.67 (dd, J 2.1 and 4.8 Hz, 1H), 3.08-2.98 (m, 3H), 2.79 (ddd, J 5.1, 14.7 and 14.7 Hz, 1H), 2.66 (ddd, J 3.9, 13.2 and 13.2 Hz, 1H), 2.45 (ddd, J 5.1, 13.2 and 13.2 Hz, 1H), 2.10 (m, 1H), 1.83 (ddd, J 2.7, 4.8 and 14.1 Hz), 1.52 (dd, J 3.3 and 14.1 Hz, 1H), 1.47 (dd, J 3.9 and 14.7 Hz, 1H). $^{13}$C NMR (D$_2$O/CF$_3$CO$_2$D) δ 211.7, 143.0, 138.6, 127.3, 122.0, 120.9, 118.5, 89.3, 69.4, 57.4, 49.2, 36.7, 34.4, 30.3, 27.5, 25.7. ES-MS m/z 288 [M+H]; HRMS $C_{16}H_{18}NO_4$ calcd for [M+H]$^+$ 288.1230, found 288.1226.

Examples 16-19

N-Demethylation of Codeine Methyl Ether (E1), Thebaine (F1), Oripavine (G1), Morphine (H1) and Dextromethorphan (J1) with Steel (Schemes 6-10: (i) m-CPBA; HCl (ii) Steel)

According to general procedure Step (i) and literature[18] procedures, N-oxidation of E1, F1, G1 and J1 with m-CPBA followed by HCl treatment afforded the N-oxide hydrochlorides E2, F2, G2, and J2, respectively.

According to the general procedure Step (i), N-oxidation of H1 (1.98 g, 6.93 mmol) with m-CPBA (2.25 g of a max 77% reagent, approx. 10.05 mmol) in $CHCl_3$ (200 mL) and MeOH (2 mL) gave, after workup employing Method B, H2 monohydrate as an off-white solid (2.50 g, 100%).

As per general procedure Step (ii), N-demethylation of E2, F2, G2, H2 and J2 using steel gave the N-nor products E3, F3, G3, H3 and J3, respectively. Results and reaction conditions are summarized in Table 2.

Physical data for the N-nor compounds E3, F3, and J3 are consistent with the literature.[18] Physical data for G3 are consistent with those given in Example 7.

Physical data for H3: $^1$H NMR (($D_2O$/$CF_3CO_2D$) δ 6.70-6.58 (m, 2H), 5.66 (d, J 9.6 Hz, 1H), 5.29 (d, J 9.6 Hz, 1H), 4.96 (d, J 5.7 Hz, 1H), 4.34-4.20 (m, 2H), 3.28 (m, 1H), 3.13-2.78 (m, 4H), 2.19 (ddd, J 4.2, 13.2 and 13.2 Hz, 1H), 2.05 (m, 1H); $^{13}$C NMR of the hydrochloride salt ($D_2O$/$CF_3CO_2D$) δ 145.5, 137.8, 133.0, 129.3, 125.7, 123.5, 118.0, 117.5, 90.7, 65.6, 51.5, 42.1, 37.1, 36.7, 31.6, 25.7; ES-MS m/z 272 [M+H]; HRMS $C_{16}H_{18}NO_3$ calcd for [M+H]$^+$ 272.1281, found 272.1286.

Examples 20-21

N-Demethylation of Tropine (K1) and Atropine (L1) with Stainless Steel (Scheme 11: (i) m-CPBA; HCl (ii) Steel)

According to the general procedure Step (i), N-oxidation employing m-CPBA, using workup Method B: tropine monohydrate (K1) (1.00 g, 6.28 mmol) gave tropine N-oxide hydrochloride monohydrate (K2) as a colorless solid (1.32 g, 99%); atropine monohydrate (L1) (429 mg, 0.72 mmol) gave atropine N-oxide hydrochloride hydrate as colorless oil (485 mg, 95%).

According to general procedure Step (ii) Method A, using workup Method A: K2 gave N-nortropine (K3), and L2 gave N-noratropine (L3). Reaction conditions and yields are given in Table 2.

N-nortropine (K3).

$^1$H NMR ($D_2O$) δ 4.11 (m, 1H), 4.00 (m, 1H), 2.39-2.30 (m, 2H), 2.20 (m, 1H), 2.14 (m, 1H), 2.08-1.90 (m, 4H); $^{13}$C NMR of the hydrochloride salt ($D_2O$) δ 62.1, 61.9, 54.1, 54.0, 35.1, 25.5; ES-MS m/z 128 [M+H]; HRMS $C_7H_{13}NO$ calcd for [M+H]$^+$ 128.1070, found 128.1065.

N-noratropine (L3).

$^1$H NMR ($D_2O$) δ 7.57-7.40 (m, 5H), 5.02 (t, J 4.2, 1H), 4.28 (dd, J 10.2 and 12.9, 1H), 4.08-3.99 (m, 2H), 3.63 (m, 1H), 3.54 (m, 1H), 2.19.1.51 (m, 8H); $^{13}$C NMR ($CDCl_3$) δ 172.3, 135.8, 128.8, 128.1, 127.7, 68.6, 63.9, 54.5, 53.1, 53.0, 37.0, 36.7, 28.8, 28.4; ES-MS m/z 276 [M+H]; HRMS $C_{16}H_{22}NO_3$ calcd for [M+H]$^+$ 276.1594, found 276.1604.

TABLE 2

Summary of N-Demethylation Reactions using Steel

| N-oxide hydrochloride (mmol) | Other additives | Solvent | Reaction conditions | Yield of 3° amine | Yield of 2° amine |
|---|---|---|---|---|---|
| A2 (0.273) | | i-PrOH | 40° C. for 17 h | (A1) 6%[a] | (A3) 62%[a] |
| B2 (0.284) | | i-PrOH | 40° C. for 22 h | (B1) 18%[a] | (B3) 53%[a] |
| B2 (0.284) | Amberlite IR-120 (Na$^+$) | i-PrOH | 40° C. for 17 h | (B1) 16%[a] | (B3) 56%[a] |
| C2 (0.272) | | i-PrOH | 40° C. for 30 h, then 50° C. for 24 h | (C1) 12%[a] | (C3) 54%[a] |
| C2 (0.272) | Amberlite IR-120 (Na$^+$) | i-PrOH | 40° C. for 18 h | (C1) 21%[a] | (C3) 75%[a] |
| D2 (0.283) | | i-PrOH | 40° C. for 72 h | (D1) 23%[a] | (D3) 66%[a] |
| E2 (0.137) | | i-PrOH | 40° C. for 48 h | (E1) 11%[b] | (E3) 88%[b] |
| F2 (0.127) | | i-PrOH | 40° C. for 48 h | (F1) 7%[b] | (F3) 86%[b] |
| G2 (0.172) | | i-PrOH | 50° C. for 120 h | (G1) 17%[b,d] | (G3) 73%[b,d] |
| H2 (4.14) | | i-PrOH | 40° C. for 96 h | (H1) 24%[a] | (H3) 71%[a] |
| H2 (0.281) | | $CHCl_3$/i-PrOH (3:1) | 50° C. for 20 h | (H1) 11%[b,d] | (H3) 86%[b,d] |
| J2 (0.154) | | i-PrOH | 40° C. for 48 h | (J1) 14%[b] | (J3) 85%[b] |
| K2 (0.472) | | i-PrOH | 80° C. for 24 h | (K1) 27%[c] | (K3) 73%[c] |
| L2 (0.286) | | i-PrOH | 40° C. for 168 h | (L1) 23%[b] | (L3) 66%[b] |
| Thevinone (0.220) | | $CHCl_3$ | RT for 40 h | (Thevinone) 26% | (N-Northevinone) 72% |
| Thevinone (0.105) | | i-PrOH | 60° C. for 6 h | (Thevinone) 14% | (N-Northevinone) 85% |

[a]General procedure Step (ii), workup Method B.
[b]General procedure Step (ii), workup Method A (Solvent system A).
[c]General procedure Step (ii), workup Method A (Solvent system B).
[d]For the column purification, no $NH_4OH$ was added to the eluant; accordingly, both the 2° and 3° amines were isolated as the corresponding hydrochloride.

N-demethylation of Tertiary N-Methylamines Using Chromium

Example 22

N-Demethylation of Oxycodone using Chromium (Scheme 4: (i) m-CPBA; HCl (ii) Chromium)

To a stirred solution of oxycodone N-oxide hydrochloride (C2) (100 mg, 0.272 mmol) in i-PrOH (10 mL) was added chromium (0) (2.6 mol equiv). The mixture was heated at 70° C. until complete (by TLC analysis). The reaction mixture was filtered and the filtrate was concentrated to dryness. To the resulting residue was added 5% HCl (30 mL) and the pH of the solution was adjusted to 7 (conc. $NH_4OH$). The solution was extracted with $CHCl_3$ (20 mL×3) and then with $CHCl_3$/MeOH (19:1, 10 mL×3); the extracts were combined and concentrated to afford oxycodone (C1). The pH of the aqueous layer was then adjusted to 9-10 using conc. $NH_4OH$ and the solution extracted with $CHCl_3$/i-PrOH (3:1). These extracts, after concentration, afforded crude N-noroxycodone (C3). Subsequent column purification of the crude N-noroxycodone, eluting with a gradient of $CHCl_3$/MeOH/$NH_4OH$ (90:10:1-85:15:1), gave pure C3. Reaction conditions and results are summarized in Table 3.

Example 23

The reaction, as described in Example 22, was repeated replacing chromium for Cr(III)Cl. Results are summarized in Table 3.

TABLE 3

Summary of N-Demethylation Reactions using Chromium

| N-oxide hydrochloride | Catalyst | Solvent | Reaction conditions | Yield of 3° amine | Yield of 2° amine |
|---|---|---|---|---|---|
| C2 (100 mg, 0.272 mmol) | Chromium (0) (2.6 equiv) | i-PrOH | 70° C. for 12 days | (C1) 14 mg[a] | (C3) 43%[b] |
| C2 (100 mg, 0.272 mmol) | Cr(III)Cl (0.2 equiv) | i-PrOH | 70° C. for 7 days | (C1) 21 mg[a] | (C3) 43%[b] |

[a]The organic extracts of the aqueous at pH 7 gave C1 as the major component (approx. 80%) along with many other impurities, by $^1$H NMR.
[b]Isolated yield after column purification.

N-Demethylation of Tertiary N-methylamines Using Iron Powder

General Procedure for N-Demethylation with Iron Powder

Scheme 15

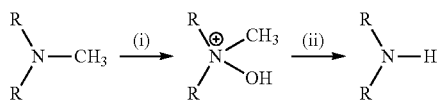

Step (i) N-Oxidation of Tertiary N-methylamine

To a stirred solution of the tertiary N-methylamine in a suitable solvent such as DCM, $CHCl_3$ or MeOH at −20° C. to −30° C. was added an oxidant such as m-CPBA or $H_2O_2$. When the reaction was complete, the N-oxide was isolated via either Method A, B or C.

Method A.

The reaction mixture was extracted with 10% NaOH to remove the m-CBA by-product. The organic layer was then washed with 1 N HCl, dried ($Na_2SO_4$), filtered, and concentrated to afford the N-oxide hydrochloride.

Method B.

The reaction mixture was extracted with 1 N HCl (×3). The extracts were combined, washed with $CHCl_3$ (×2) and concentrated to afford the desired N-methylamine N-oxide hydrochloride.

Method C:

Ice water was added to the reaction mixture and the layers separated. The pH of the aqueous layer was adjusted to 2 (6 N HCl), extracted with $CHCl_3$ (×4) and then with $CHCl_3$/i-PrOH (3:1). The latter extracts were dried, filtered and concentrated to afford the N-oxide hydrochloride.

Step (ii) N-Demethylation of the Tertiary N-methylamine N-oxide Hydrochloride with Iron Powder Method A:

To a stirred solution of the tertiary N-methylamine N-oxide hydrochloride (0.27 mmol) in a solvent such as MeOH, EtOH, i-PrOH or $CHCl_3$ (10 mL) was added iron powder (0.1-2.5 equivalents). The mixture was either stirred at room temperature or heated at 40-60° C. until reaction was complete. The reaction mixture was filtered (celite) and the filter pad washed with $CHCl_3$/MeOH (4:1, 10 mL×2). The original filtrate and washings were combined and concentrated to dryness to give a crude mixture of the N-nor compound and the starting tertiary N-methylamine. Pure N-nor compound was isolated either via column chromatography on $SiO_2$ [eluting with a gradient of $CHCl_3$/MeOH/$NH_4OH$ (90:10:1-85:15:1; solvent system A) or with ethyl acetate/MeOH/$NH_4OH$ (60:40:1; solvent system B)] (workup Method A) or via extraction of an aqueous solution of the crude at different pH's with a suitable solvent (workup Method B). For example, after removal of the volatiles, 5% HCl (approx. 30 mL for 0.27 mmol) was added to the crude reaction mixture. The pH of the solution was adjusted to 7 (conc. $NH_4OH$) and the solution was extracted with $CHCl_3$ (20 mL×3) and then with $CHCl_3$/MeOH (19:1, 10 mL×3). These extracts were combined and concentrated to afford the starting tertiary N-methylamine. The pH of the aqueous layer was then adjusted to 9-10 using conc. $NH_4OH$ and the solution extracted with $CHCl_3$ or $CHCl_3$/i-PrOH (3:1). These extracts, after concentration, afforded the N-nor compound.

Method B:

N-Demethylation of the tertiary N-methylamine N-oxide hydrochloride was conducted with iron powder as described above, with the addition of 0.5-1.0 g of Amberlite IR-120 ($Na^+$) resin. When the reaction was complete, the reaction mixture was filtered (celite) and the filter pad washed with $CHCl_3$/MeOH (4:1, 10 mL×2). The original filtrate and washings were combined and subsequently processed as described above.

Method C:

N-Demethylation of the tertiary N-methylamine N-oxide hydrochloride with iron powder (one equivalent) was carried out according to Method A, with the addition of an inorganic salt.

Specification for Iron Powder Used

| Supplier | Physical properties | Chemical analysis (%) | | | | | | |
|---|---|---|---|---|---|---|---|---|
| | | Fe | Cr | Ni | Mo | Mn | Si | Other |
| Höganäs Sweden | Powder, +212 to −45 microns | 99 | 0.002 | 0.01 | <5 ppm | 0.04 (MnO) | 0.13 ($SiO_2$) | Bal |

Example 24

N-Demethylation of Oxycodeinone (A1), Oxymorphinone (B1), Oxycodone (C1), Oxymorphone (D1), Codeine Methyl Ether (E1), Thebaine (F1), Oripavine (G1), Morphine (H1), Dextromethorphan (J1), Tropine (K1) and Atropine (L1) with Iron Powder (Scheme 15: (i) m-CPBA; HCl (ii) Iron Powder)

According to the general procedure Step (i), using workup Method B, N-oxidation of A1-D1, G1, H1, K1 and L1 gave the N-oxide hydrochlorides A2-D2, G2, H2, K2 and L2, respectively. The N-oxide hydrochlorides E2, F2 and J2 were from E1, F1 and J1, respectively, according to literature[18] procedures.

As per general procedure Step (ii) Method A/B, treatment of A2-H2 and K2-J2 with iron powder gave the N-nor products A3-H3 and K3-J3, respectively. Results and reaction conditions are summarized in Table 4.

Physical data for the N-nor compounds A3-D3, G3, H3, K3 and L3 are consistent with those previously reported in Examples 1-4, 7, 8, 10 and 11, respectively; physical data for the N-nor compounds E3, F3 and J3 are consistent with the literature.[18]

Example 25

N-Demethylation of Tertiary N-Methylamines Using Iron Powder and an Inorganic Salt; Dextromethorphan N-Oxide Hydrochloride (J2) was Employed as Representative Substrate

According to general procedure Step (ii) Method C, a solution of dextromethorphan N-oxide hydrochloride (J2) (100 mg, 0.309 mmol) in MeOH (10 mL) was treated with iron powder and $CuSO_4 \cdot 5H_2O$. Subsequent workup followed by purification via column chromatography gave J1 and J3.

The above reaction was repeated substituting $CuSO_4 \cdot 5H_2O$ with other inorganic salts. Results are summarized in Table 5.

TABLE 5

Summary of Iron Powder-mediated N-Demethylation of Dextromethorphan N-oxide Hydrochloride (J2)[a] in the presence of added Salts[b]

| Added salt | Time (h) | % Isolated yield[c] J3 | J1 | J2 |
|---|---|---|---|---|
| — | 120 | 58 | 21 | 9 |
| $CuSO_4 \cdot 5H_2O$ | 6 | 81 | 12 | — |

TABLE 4

Summary of N-Demethylation Reactions of using Iron Powder

| N-oxide hydrochloride (mmol) | Iron powder (equiv) | Other additives | Solvent | Reaction conditions | Yield of 3° amine | Yield of 2° amine |
|---|---|---|---|---|---|---|
| A2 (0.547) | 1 | | i-PrOH | 40° C. for 27 h | (A1) 26%[a] | (A3) 46%[a] |
| B2 (0.284) | 0.5 | | i-PrOH | 40° C. for 7 days | (B1) 44%[a] | (B3) 40%[a] |
| B2 (0.284) | 1 | Amberlite IR-120 (Na+) | i-PrOH | 40° C. for 1 h | (B1) 39%[a] | (B3) 37%[a] |
| C2 (0.272) | 2 | | i-PrOH | 60° C. for 22 h | (C1) 26%[a] | (C3) 55%[a] |
| C2 (0.272) | 2 | Amberlite IR-120 (Na+) | i-PrOH | 60° C. for 2 h | (C1) 17%[b] | (C3) 57%[b] |
| D2 (0.283) | 0.5 | | i-PrOH | 40° C. for 72 h | (D1) 41%[a] | (D3) 42%[a] |
| E2 (0.137) | 1 | | i-PrOH | 40° C. for 48 h | (E1) 7%[b] | (E3) 88%[b] |
| E2 (0.137) | 1 | | CHCl$_3$ | RT for 2 h | (E1) 1%[b] | (E3) 97%[b] |
| F2 (0.137) | 1.3 | | CHCl$_3$ | RT for 1 h | (F1) 13%[b] | (F3) 86%[b] |
| G2 (0.143) | 2.5 | Amberlite IR-120 (Na+) | i-PrOH | 40° C. for 3 h | (G1) 27%[b,d] | (G3) 65%[b,d] |
| H2 (0.281) | 0.5 | | i-PrOH | 40° C. for 24 h | (H1) 36%[b,d] | (H3) 58%[b,d] |
| J2 (0.309) | 1 | | CHCl$_3$ | RT for 1 h | (J1) nd[e] | (J3) 97%[b] |
| J2 (0.309) | 0.25 | | i-PrOH | RT for 24 h | (J1) 8[b] | (J3) 88%[b] |
| K2 (0.472) | 1 | | i-PrOH | 60° C. for 2 h | (K1) 5%[c] | (K3) 84%[c] |
| L2 (0.247) | 0.5 | | i-PrOH | 40° C. for 6 h | (L1) 16%[b] | (L3) 69%[b] |

[a]General procedure Step (ii), workup Method B.
[b]General procedure Step (ii), workup Method A (Solvent system A).
[c]General procedure Step (ii), workup Method A (Solvent system B).
[d]For the column purification, no NH$_4$OH was added to the eluant; accordingly, G1 and G3 were isolated as the corresponding hydrochlorides.
[e]Not detected TABLE 5-continued Summary of Iron Powder-mediated N-Demethylation
of Dextromethorphan N-oxide Hydrochloride (J2)[a]
in the presence of added Salts[b]

| Added salt | Time (h) | % Isolated yield[c] | | |
|---|---|---|---|---|
| | | J3 | J1 | J2 |
| $ZnSO_4 \cdot 7H_2O$ | 120 | 81 | 9 | 9 |
| $CuCl_2$ | 120 | 54 | 40 | 4 |
| CuCl | 120 | 47 | 33 | 18 |
| $Cu(NO_3)_2 \cdot 2\frac{1}{2}H_2O$ | 120 | 38 | 55 | 7 |
| $Co(NO_3)_2 \cdot 6H_2O$ | 120 | 56 | 43 | — |

[a] MeOH was employed as representative solvent; concentration: 10 mL per 100 mg of N-oxide.
[b] Reactions were conducted at room temperature with one equivalent of iron powder and 0.25 equivalents of added salt.
[c] Isolated yield via column chromatography.

Example 26

N-Demethylation of Dextromethorphan (J1) m-CPBA and Iron Powder

To a stirred mixture of dextromethorphan (89 mg, 0.328 mmol), iron powder (37 mg, 0.661 mmol) and MeOH (10 mL) was added m-CPBA (max. 77% reagent, 1.312 mmol). When the intermediate N-oxide J2 was completely consumed (via TLC analysis), the mixture was filtered through celite. The filter pad was washed with $CHCl_3$ (5 mL×2); the filtrate and washings were combined and concentrated. To the remaining residue was added $CHCl_3$ (50 mL) and the solution washed with 10% aqueous NaOH (5 mL×2), dried ($Na_2SO_4$), filtered and concentrated to give a crude mixture of dextromethorphan (J1) and the N-nor compound J3. Pure N-nor-dextromethorphan (J3) was isolated via column chromatography on $SiO_2$, eluting with a gradient of $CHCl_3$/MeOH/$NH_4OH$ (90:10:1-85:15:1). Results are summarized in Table 6.

Example 27

N-Demethylation of Thebaine (F1) with m-CPBA and Steel

To a stirred suspension of thebaine (195 mg, 0.642 mmol) in i-PrOH (20 mL) at −10° C. was added m-CPBA (max. 77% reagent, 0.642 mmol) portionwise over 20 min. When conversion to the N-oxide F2 was complete, as analysed by TLC analysis, concentrated hydrochloric acid (0.061 mL of 32% w/w) was added dropwise. To the resulting clear colorless solution was added steel (3.2 g) and the reaction mixture was heated at 55-60° C. until complete consumption of the intermediate N-oxide F2 (via TLC analysis). Unreacted steel was retrieved from the reaction mixture and the mixture concentrated to dryness. To remaining residue was added $CHCl_3$ (80 mL) and the resulting solution washed with 10% aqueous NaOH (5 mL×2), dried ($Na_2SO_4$), filtered and concentrated. Subsequent column purification on $SiO_2$, eluting with $CHCl_3$/MeOH/$NH_4OH$ (98:2:1-95:5:1) afforded first thebaine (F1) and then N-northebaine (F3). Reaction conditions and yields are summarized in Table 6.

Example 28

N-Demethylation of Thebaine (F1) with m-CPBA and Iron Powder

The reaction according to Example 27 was repeated starting with thebaine (195 mg, 0.642 mmol) substituting steel with iron powder (72 mg, 1.287 mmol). No concentrated hydrochloric acid was added to the reaction mixture. Reaction mixture was stirred at 50° C. for 4 days. Results are summarized in Table 6.

Example 29

N-Demethylation of Thebaine (F1) with m-CPBA in the Presence of Iron Powder

To a stirred mixture of thebaine (195 mg, 0.642 mmol), iron powder (72 mg, 1.287 mmol) and i-PrOH (20 mL) at −10° C. was added m-CPBA (max. 77% reagent, 0.642 mmol). When conversion of thebaine into the intermediate N-oxide F2 was complete (via TLC analysis), concentrated hydrochloric acid (0.061 mL of 32% w/w) was added dropwise. The reaction mixture was heated at 50° C. until complete consumption of the intermediate N-oxide F2 (via TLC analysis). The mixture was cooled and filtered through celite. The filter pad was washed with $CHCl_3$ (5 mL×2) and the washings combined with the original filtrate and concentrated. Subsequent workup was according to Example 27. Results are summarized in Table 6.

TABLE 6

One-Pot N-Demethylation of N-Methyl Heterocycles

| Ex. | N-methyl heterocycle (mmol) | Catalyst (equiv) | m-CPBA (equiv) | Conc. HCl (equiv) | Solvent | Reacn condtns | 2° amine | 3° amine |
|---|---|---|---|---|---|---|---|---|
| 26 | Dextro-methorphan (0.328) | Fe (2) | 4 | — | MeOH | RT, 3 days | 67% (J3) | 16% (J1) |
| 27 | Thebaine (0.642) | Stainless steel (excess) | 1 | 1 | i-PrOH | 55-60° C., 16 h | 80% (F3) | 17% (F1) |
| 28[1] | Thebaine (0.642) | Fe (2) | 1 | — | i-PrOH | 50° C., 4 days | 43% (F3) | 30% (F1) |
| 29[2] | Thebaine (0.642) | Fe (2) | 1 | 1 | i-PrOH | 50° C., 20 h | 48% (F3) | 26%[3] (F1) |

[1] Iron powder was added subsequent to the formation of the intermediate N-oxide.
[2] Iron powder was added prior to the formation of the intermediate N-oxide.
[3] Approximately 90% pure by $^1$H NMR.

Example 30

Effect of Stoichiometry, Temperature and/or Solvents on N-Demethylation Reactions of Tertiary N-Methylamines with Iron Powder Under a Nitrogen or Inert Atmosphere; Oripavine (G1) was Employed as Representative Substrate According to the general procedure Step (i), oripavine (G1) and m-CPBA gave, after workup Method C, Oripavine N-oxide hydrochloride (G2).

According to general procedure Step (ii), Method A, a mixture of oripavine N-oxide hydrochloride (G2) (100 mg, 0.286 mmol), iron powder (0.5 equiv) and degassed i-PrOH (10 mL) was stirred at 40° C. under nitrogen until complete consumption of starting material (as analyzed by TLC analysis). The reaction mixture was concentrated to dryness to give a crude mixture of oripavine and N-nororipavine hydrochlorides. Subsequent column chromatography of the crude mixture on $SiO_2$ [eluting with a gradient of $CHCl_3$/MeOH (24:1-17:3)] isolated N-nororipavine (G3) from oripavine (G1), both as the corresponding hydrochloride.

The above reaction was repeated varying either the stoichiometry of iron powder, temperature and/or solvents. Results are summarized in Table 7.

TABLE 7

Summary of N-Demethylation Reactions of Oripavine (G1) with Iron Powder under a Nitrogen Atmosphere[a]

| | | | | | % Yield[d] | |
|---|---|---|---|---|---|---|
| Entry | Iron powder (equiv) | Solvent[b,c] | Temp (° C.) | Time (h) | N-Nororipavine (G3) | Oripavine (G1) |
| 1 | 0.5 | i-PrOH | 40 | 48 | 53 | 25 |
| 2 | 0.25 | i-PrOH | 40 | 144 | 65 | 25 |
| 3 | 0.5 | i-PrOH | 60 | 16 | 52 | 29 |
| 4 | 2 | $CHCl_3$/i-PrOH (1:1) | 40 | 48 | 57 | 20 |
| 5 | 0.5 | $CHCl_3$/i-PrOH (1:1) | 40 | 3 | 71 | 25 |
| 6 | 2 | $CHCl_3$/i-PrOH (3:1) | 40 | 44 | 70 | 25 |
| 7 | 0.5 | $CHCl_3$/i-PrOH (3:1) | 40 | 5.5 | 70 | 25 |
| 8 | 0.5 | $CHCl_3$/i-PrOH (3:1) | RT | 5.5 | 75 | 23 |
| 9 | 0.5 | $CHCl_3$/i-PrOH (3:1) | 60 | 4 | 65 | 25 |
| 10 | 0.5 | $CHCl_3$/i-PrOH (9:1) | 40 | 168 | 58 | 23 |

[a]Results in Table are for Step (ii) of the N-demethylation Reaction.
[b]Reactions employed degassed solvents.
[c]Concentration: 10 mL of solvent per 100 mg of substrate.
[d]Isolated via column chromatography.

Example 31

N-Demethylation Reactions of Tertiary N-Methylamines with Iron Powder in Air or in the Presence of Oxygen; Oripavine (G1) was Employed as Representative Substrate The reactions as described in Example 30 were conducted in air rather than under nitrogen. Results are summarized in Table 8.

TABLE 8

Summary of N-Demethylation Reactions of Oripavine (G1) with Iron Powder in Air[a]

| | | | | | % Yield[c] | |
|---|---|---|---|---|---|---|
| Entry | Iron powder (equiv) | Solvent[b] | Temp (° C.) | Time (h) | N-Nororipavine (G3) | Oripavine (G1) |
| 1 | 2 | i-PrOH | 40 | 16 | 67 | 24 |
| 2 | 0.5 | i-PrOH | 40 | 16 | 67 | 31 |
| 3 | 0.25 | i-PrOH | 40 | 120 | 73 | 26 |
| 4 | 10 | i-PrOH | 40 | 16 | 64 | 29 |
| 5 | 10 | i-PrOH | 60 | 48 | 54 | 37 |
| 6 | 0.5 | i-PrOH | 60 | 16 | 60 | 25 |
| 7 | 0.5 | i-PrOH | RT | 168 | 76 | 19 |
| 8 | 0.5 | $CHCl_3$/i-PrOH (3:1) | 40 | 2 | 74 | 24 |
| 9 | 0.5 | $CHCl_3$/i-PrOH (9:1) | 40 | 16 | 60 | 22 |
| 10 | 0.5 | $CHCl_3$/i-PrOH (3:1) | RT | 3.5 | 75 | 22 |
| 11 | 0.5 | $CHCl_3$/i-PrOH (3:1) | 60 | 1 | 71 | 21 |

[a]Results in Table are for Step (ii) of the N-demethylation Reaction.
[b]Concentration: 10 mL of solvent per 100 mg of substrate.
[d]Isolated via column chromatography N-demethylation of Tertiary N-Methylamines Using Stainless Steel; Further Examples of N-demethylation of Tertiary N-methylamines Using Steel and Iron Alloys

Example 32

N-Demethylation Reactions of Tertiary N-Methylamines with Iron Alloys, Steel or Stainless Steel The reactions as described in Examples 30/31 were conducted replacing the iron powder with iron alloys, steel or stainless steel (see Table 9 for some examples of iron catalysts). Oripavine (G1) was employed as representative substrate. Results are summarized in Table 10.

TABLE 9

Examples of Iron Catalysts used

| Iron powder/ alloy/steel/ stainless steel | Supplier | Physical properties | Chemical analysis (%) | | | | | | |
|---|---|---|---|---|---|---|---|---|---|
| | | | Fe | Cr | Ni | Mo | Mn | Si | Other |
| Iron(0) | Höganäs Sweden | Powder, +212 to −45 microns | 99 | 0.002 | 0.01 | <5 ppm | 0.04 (MnO) | 0.13 ($SiO_2$) | Bal |

TABLE 9-continued

Examples of Iron Catalysts used

| Iron powder/alloy/steel/stainless steel | Supplier | Physical properties | Chemical analysis (%) | | | | | | |
|---|---|---|---|---|---|---|---|---|---|
| | | | Fe | Cr | Ni | Mo | Mn | Si | Other |
| 302 | Alfa Aesar | Spheres, 1 mm dia | 70 | 18 | 9 | | 2 | 1 | |
| 303-L | Alfa Aesar | Powder, −140 mesh | 70 | 17 | 13 | | | | |
| 304-L | Alfa Aesar | Powder, −100 mesh | 70 | 19 | 11 | | | | |
| 316-L | Alfa Aesar | Powder, −100 mesh | 67.5 | 17 | 13 | 2.5 | | | |
| 410-L | Alfa Aesar | Powder, −100 mesh, annealed | 87.5 | 12.5 | | | | | |
| Astaloy CrL | Höganäs Sweden | Powder, +212 to −45 microns | Bal | 1.47 | | 0.19 | | | 0.002 (C) |
| Astaloy CrM | Höganäs Sweden | Powder, +212 to −45 microns | Bal | 2.85 | | 0.46 | | | 0.004 (C) |
| Steel shots | Alfa Aesar | Non-spherical, 0.25 mm dia | 97.1 | | | | 0.35-1.2 | 0.4 max | 0.8-1.2 (C) |

TABLE 10

Summary of N-Demethylation Reactions of Tertiary N-Methylamines with Iron Alloys/Steel/Stainless Steels: Oripavine (G1) was employed as a representative substrate[a,b]

| Entry | Iron alloy/steel/ stainless steel (equiv) | Solvent[c] | Temp (° C.)/ Atmosphere | Time (h) | % Yield[d] | |
|---|---|---|---|---|---|---|
| | | | | | N-Nororipavine (G3) | Oripavine (G1) |
| 1A | 303-L (10) | CHCl$_3$/i-PrOH (3:1) | 40/N$_2$ | 96 | 77 | 22 |
| 1B | 303-L (0.5) | CHCl$_3$/i-PrOH (1:1) | 40/N$_2$ | 27 | 79 | 11 |
| 1C | 303-L (0.5) | CHCl$_3$/i-PrOH (3:1) | 40/N$_2$ | 96 | 79 | 17 |
| 1D | 303-L (0.5) | CHCl$_3$/i-PrOH (3:1) | 40/AIR | 16 | 81 | 18 |
| 1E | 303-L (0.5) | CHCl$_3$/i-PrOH (9:1) | 40/AIR | 30 | 81 | 17 |
| 1F | 303-L (0.5) | CHCl$_3$/i-PrOH (3:1) | 60/N$_2$ | 40 | 81 | 17 |
| 1G | 303-L (0.5) | CHCl$_3$/i-PrOH (3:1) | 60/AIR | 48 | 75 | 22 |
| 1H | 303-L (0.5) | CHCl$_3$/i-PrOH (3:1) | RT/N$_2$ | 480 | 82 | 16 |
| 1J | 303-L (0.5) | CHCl$_3$/i-PrOH (3:1) | RT/AIR | 48 | 81 | 18 |
| 1K | 303-L (0.5) | i-PrOH | 40/AIR | 96 | 66 | 30 |
| 2 | 304-L (0.5) | CHCl$_3$/i-PrOH (3:1) | 40/AIR | 168 | 76 | 20 |
| 3A | 316-L (0.5) | CHCl$_3$/i-PrOH (3:1) | 40/AIR | 336 | 70 | 27 |
| 3B | 316-L (0.5) | CHCl$_3$/i-PrOH (3:1) | 60/AIR | 264 | 72 | 27 |
| 3C | 316-L (10) | CHCl$_3$/i-PrOH (3:1) | 60/AIR | 48 | 70 | 29 |
| 3D | 316-L (10) | CHCl$_3$/i-PrOH (3:1) | 60/N$_2$ | 96 | 67 | 30 |
| 4 | 302 (0.5) | CHCl$_3$/i-PrOH (3:1) | 40/AIR | 600 | 71 | 26 |

TABLE 10-continued

Summary of N-Demethylation Reactions of Tertiary N-Methylamines with Iron Alloys/Steel/Stainless Steels: Oripavine (G1) was employed as a representative substrate[a,b]

| Entry | Iron alloy/steel/ stainless steel (equiv) | Solvent[c] | Temp (° C.)/ Atmosphere | Time (h) | % Yield[d] N-Nororipavine (G3) | Oripavine (G1) |
|---|---|---|---|---|---|---|
| 5A | 410-L (10) | CHCl$_3$/i-PrOH (3:1) | 60/N$_2$ | 384 | 37 | 36 |
| 5B | 410-L (0.5) | CHCl$_3$/i-PrOH (3:1) | 40/AIR | 84 | 79 | 16 |
| 6 | CrL (0.5) | i-PrOH | 40/AIR | 48 | 69 | 20 |
| 7A | CrM (0.5) | CHCl$_3$/i-PrOH (3:1) | 40/AIR | 16 | 65 | 18 |
| 7B | CrM (0.5) | i-PrOH | 40/AIR | 48 | 67 | 22 |
| 8A | Steel shots (10) | CHCl$_3$/i-PrOH (3:1) | 60/N$_2$ | 168 | 45 | 36 |
| 8B | Steel shots (0.5) | CHCl$_3$/i-PrOH (3:1) | 40/AIR | 16 | 69 | 14 |

[a]Results in Table are for Step (ii) of the N-demethylation Reaction.
[b]Reactions conducted under nitrogen employed degassed solvents.
[c]Concentration: 10 mL of solvent per 100 mg of substrate.
[d]Isolated via column chromatography Example 33

N-Demethylation Reactions of Tertiary N-Methylamines Using Iron Catalysts with an Added Ferric Salt According to Examples 30-32, Step (ii) of N-demethylation reactions of tertiary N-methylamines with iron powder, iron alloys, steel or stainless steel were conducted with an added ferric salt such as ferric chloride hexahydrate. Oripavine (G1) was employed as representative substrate. Results are summarized in Table 11.

TABLE 11

Summary of N-Demethylation Reactions of Oripavine (G1) with Iron Catalysts and an added Ferric Salt such as Ferric Chloride Hexahydrate[a,b]

| Entry | Iron powder/ iron alloy/ steel/ stainless steel (equiv) | FeCl$_3$•6H$_2$O (equiv) | Solvent[c] | Temp (° C.)/ Atmosphere | Time | % Yield[d] N-Nororipavine (G3) | Oripavine (G1) |
|---|---|---|---|---|---|---|---|
| 1 | 303-L (0.5) | 0.025 | CHCl$_3$/i-PrOH (3:1) | RT/AIR | 16 h | 81 | 17 |
| 2 | 303-L (0.5) | 0.25 | CHCl$_3$/i-PrOH (3:1) | RT/AIR | 72 h | 74 | 22 |
| 3 | CrM (0.5) | 0.025 | CHCl$_3$/i-PrOH (3:1) | 40/AIR | 60 min | 76 | 22 |
| 4 | 316-L (0.5) | 0.025 | CHCl$_3$/i-PrOH (3:1) | 40/AIR | 48 h | 79 | 21 |
| 5 | Fe(0) (0.5) | 0.025 | CHCl$_3$/i-PrOH (3:1) | RT/AIR | 70 min | 77 | 19 |
| 6 | Fe(0) (0.5) | 0.025 | CHCl$_3$/i-PrOH (3:1) | RT/N$_2$ | 3.5 h | 78 | 20 |
| 7 | Fe(0) (0.13) | 0.025 | CHCl$_3$/i-PrOH (3:1) | RT/AIR | 4 h | 81 | 17 |
| 8 | Fe(0) (0.13) | 0.13 | CHCl$_3$/i-PrOH (3:1) | RT/AIR | 2 h | 76 | 21 |

TABLE 11-continued

Summary of N-Demethylation Reactions of Oripavine (G1) with Iron
Catalysts and an added Ferric Salt such as Ferric Chloride Hexahydrate[a,b]

| Entry | Iron powder/ iron alloy/ steel/ stainless steel (equiv) | $FeCl_3 \cdot 6H_2O$ (equiv) | Solvent[c] | Temp (° C.)/ Atmosphere | Time | % Yield[d] N-Nororipavine (G3) | Oripavine (G1) |
|---|---|---|---|---|---|---|---|
| 9 | Fe(0) (0.5) | 0.025 | i-PrOH | RT/AIR | 168 h | 74 | 21 |
| 10 | 303-L (0.5) | 0.25 | $CHCl_3$/i-PrOH (3:1) | RT/AIR | 72 h | 74 | 22 |

[a]Results in Table are for Step (ii) of the N-demethylation Reaction.
[b]Reactions conducted under nitrogen employed degassed solvents.
[c]Concentration: 10 mL of solvent per 100 mg of substrate.
[d]Isolated via column chromatography.

Example 34

One-Pot N-Demethylation of Oripavine (G1) with m-CPBA and Iron Catalyst with an Added Ferric Salt To a stirred solution of oripavine (1.00 g, 3.36 mmol) in $CHCl_3$/i-PrOH (3:1, 100 mL) at −25° C. was added m-CPBA (max. 77% reagent, 3.36 mmol) portionwise over 15 min. The reaction mixture was allowed to warm to −5° C. over 15 min, stirred for a further 15 min and then cooled to −20° C. Concentrated HCl (0.3 mL) was then added followed by stainless steel 303-L powder (94 mg) and $FeCl_3 \cdot 6H_2O$ (23 mg). The mixture was allowed to warm to RT and stirred in air until complete consumption of the intermediate N-oxide G2 (via TLC analysis). All volatiles were then removed in vacuo; $H_2O$ (100 mL) was added and the mixture was extracted with $CHCl_3$ (50 mL×4). The aqueous phase was saturated with NaCl before extraction with $CHCl_3$/i-PrOH (3:1, 100 mL×3, 50 mL×2). The latter extracts were combined, dried ($Na_2SO_4$), filtered and concentrated. The remaining residue was purified via column chromatography on silica, eluting with a gradient of $CHCl_3$/i-PrOH (24:1-17:3) which afforded oripavine (0.21 g, 19%) and N-nororipavine (G3) (0.77 g, 72%), both as the corresponding hydrochloride salt.

Examples of iron catalysts that may be employed in the reaction as described in Example 34 include, but are not limited to, iron powder, iron alloys, steel and other stainless steels (see Table 9 for examples) and galvanized iron.

The method according to Example 34 may also be conducted with stainless steel 303-L or other iron catalysts, with or without addition of a ferric salt and/or under an inert atmosphere, in air or in the presence of oxygen, at a different temperature and/or using a different solvent or solvent mixture (see Tables 7, 8, 10 and 11 for examples of some reaction conditions).

REFERENCES

1 D. S. Fries in *Foye's Principles of Medicinal Chemistry*. 5th Ed. (Eds.: D. A. Williams & T. L. Lemke), Lippincott William & Wilkins, Philadelphia, 2002.
2 J. von Braun, *Chem. Ber.* 1909, 42, 2035.
3 (a) J. H. Cooley, E. J. Evain, *Synthesis* 1989, 1. (b) K. C. Rice, *J. Org. Chem.* 1975, 40, 1850. (c) K. C. Rice, E. L. May, *J. Heterocycl. Chem.* 1977, 14, 665.
4 (a) L. S. Schwab, *J. Med. Chem.* 1980, 23, 698. (b) H. Merz, K. H. Pook, *Tetrahedron* 1970, 26, 1727.
5 J. A. Ripper, E. R. T. Tiekink, P. J. Scammells, *Bioorg. Med. Chem. Lett.* 2001, 11, 443.
6 (a) P. J. Smith, C. K. Mann, *J. Org. Chem.* 1969, 34, 1821. (b) J. E. Barry, M. Finkelstein, E. A. Mayeda, S. D. Ross, *J. Org. Chem.* 1974, 39, 3488.
7 (a) K. M. Madyastha, *Proc. Indian Acad. Sci.* 1994, 106, 1203. (b) K. M. Madyastha, G. V. B. Reddy, *J. Chem. Soc., Perkin Trans.* 1 1994, 911.
8 (a) K. McCamley, J. A. Ripper, R. D. Singer, P. J. Scammells, *J. Org. Chem.* 2003, 68, 9847-9850. (b) S. Thavaneswaran, P. J. Scammells, *Bioorg. Med. Chem. Lett.* 2006, 16, 2868-2871.
9 S. Thavaneswaran, K. McCamley, P. J. Scammells, *Nat. Prod. Commun.* 2006, 1(10), 885-897.
10 Carrol et al, *Adv. Synth. Catal.* 2008, 350, 2984-2992
11 WO 2009/003272
12 V. Chaudhary et al, *Collectl. Czech. Chem. Commun.* 2009, 74(7-8), 1179-1193.
13 S. Berényi et al, *Current Medicinal Chemistry*, 2009, 16, 3215-3242
14 *Protective Groups in Organic Synthesis*, T. W. Greene and P Wutz, John Wiley and Son, 2nd Edition (1991).
15 J. P. Ferris, R. D. Gerwe, G. R. Gapsi, *J. Am. Chem. Soc.* 1967, 89, 5270-5275.
16 A. Zhang, C. Csutoras, R. Zong and J. L. Neumeyer, *Org. Lett.* 2005, 7(15), 3239-3242.
17 I. Iijima, J. Minamikawa, A. E. Jacobson, A. Brossi and K. C. Rice, *J. Med. Chem.* 1978, 21(4), 398-400.
18 G. B. Kok, T. D. Ashton, P. J. Scammells, *Adv. Synth. Catal.* 2009, 351 (1-2), 283-286.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:
1. A method of N-demethylating an N-methylated heterocycle, said method comprising the steps of:
(i) oxidizing an N-methylated heterocycle to form an N-methyl, N-oxide heterocycle, and
(ii) exposing the N-methyl, N-oxide heterocycle to a transition metal with an oxidation state of zero;

wherein the N-methylated heterocycle is an N-methyl morphine alkaloid or an N-methyl tropane alkaloid.

2. The method according to claim 1 wherein step (i) is performed by exposing the N-methyl, N-oxide heterocycle to an oxidizing agent selected from the group consisting of m-chloroperbenzoic acid and hydrogen peroxide.

3. A method of preparing an N-demethylated heterocycle from an N-methyl, N-oxide heterocycle, the method comprising:
   (i) providing an N-methyl, N-oxide heterocycle formed from an N-methylated heterocycle; and
   (ii) exposing the N-methyl, N-oxide heterocycle to a transition metal with an oxidation state of zero;
wherein the N-methylated heterocycle is an N-methyl morphine alkaloid or an N-methyl tropane alkaloid.

4. The method according to claim 3, wherein the N-methylated heterocycle is an N-methyl morphine alkaloid.

5. The method according to claim 4 wherein the N-methyl morphine alkaloid has a 6,8-diene system.

6. The method according to claim 3, wherein a ferric salt is added to step (ii).

7. The method according to claim 3, wherein step (ii) is conducted in the presence of oxygen.

8. The method according to claim 3, wherein step (ii) is conducted under an inert atmosphere.

9. The method according to claim 3, wherein the N-methyl, N-oxide heterocycle is isolated before exposure to the transition metal.

10. The method according to claim 3, wherein the transition metal is Fe(0) in the form of the elemental metal or as part of an alloy.

11. The method according to claim 10 wherein the alloy is stainless steel.

12. The method according to claim 3, wherein ferrocene, a substituted derivative thereof, or Cr(III) is substituted for the transition metal having an oxidation state of zero.

13. A method of preparing a non-methyl N-substituted heterocycle, the method comprising: preparing an N-demethylated heterocycle according to claim 3; treating the N-demethylated heterocycle with a compound of formula R-L, where R is a selected from the group consisting of straight chain, branched and cyclic isomers of $C_{2-6}$alkyl, $C_{2-6}$alkenyl and $C_{2-6}$alkynyl, and L is a leaving group, under such conditions such that the nitrogen of the heterocycle is substituted with R.

14. The method according to claim 1, wherein the N-methylated heterocycle is an N-methyl morphine alkaloid.

15. The method according to claim 14, wherein the N-methyl morphine alkaloid has a 6,8-diene system.

16. The method according to claim 1, wherein the N-methylated heterocycle is an N-methyl tropane alkaloid.

17. The method according to claim 1, wherein the N-methyl, N-oxide heterocycle is isolated before exposure to the transition metal.

18. The method according to claim 1, wherein ferrocene, a substituted derivative thereof, or Cr(III) is substituted for the transition metal having an oxidation state of zero.

19. A method of preparing a non-methyl N-substituted heterocycle, the method comprising: preparing an N-demethylated heterocycle according to claim 1; treating the N-demethylated heterocycle with a compound of formula R-L, where R is selected from the group consisting of straight chain, branched and cyclic isomers of $C_{2-6}$alkyl, $C_{2-6}$alkenyl and $C_{2-6}$alkynyl, and L is a leaving group, under such conditions such that the nitrogen of the heterocycle is substituted with R.

20. The method according to claim 3, wherein the N-methylated heterocycle is an N-methyl tropane alkaloid.

* * * * *